US012625130B2

(12) United States Patent
Boyanov et al.

(10) Patent No.: US 12,625,130 B2
(45) Date of Patent: May 12, 2026

(54) NANOPORE SENSOR DEVICES

(71) Applicant: ILLUMINA, INC., San Diego, CA (US)

(72) Inventors: Boyan Boyanov, San Diego, CA (US); Jeffrey G. Mandell, San Diego, CA (US); Seth M. McDonald, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 249 days.

(21) Appl. No.: 18/553,192

(22) PCT Filed: Mar. 1, 2022

(86) PCT No.: PCT/US2022/018371
§ 371 (c)(1),
(2) Date: Sep. 28, 2023

(87) PCT Pub. No.: WO2022/211951
PCT Pub. Date: Oct. 6, 2022

(65) Prior Publication Data
US 2024/0377380 A1      Nov. 14, 2024

Related U.S. Application Data

(60) Provisional application No. 63/168,646, filed on Mar. 31, 2021.

(51) Int. Cl.
*G01N 33/487* (2006.01)
*B82B 1/00* (2006.01)
(Continued)

(52) U.S. Cl.
CPC ....... *G01N 33/48721* (2013.01); *B82B 1/008* (2013.01); *B82B 3/0038* (2013.01); *C12Q 1/6869* (2013.01)

(58) Field of Classification Search
None
See application file for complete search history.

(56) References Cited

U.S. PATENT DOCUMENTS

| 5,795,782 A | 8/1998 | Church et al. |
| 7,163,658 B2 | 1/2007 | Benison |
| | (Continued) | |

FOREIGN PATENT DOCUMENTS

| CA | 2698876 A1 | 3/2009 |
| CA | 3001621 A1 | 5/2017 |
| | (Continued) | |

OTHER PUBLICATIONS

Cornelius et al., "Cation complexation by valinomycin- and nigericin-type inophores registered by the fluorescence signal of Tl+", Biochemistry. Jul. 16, 1974;13(15):3052-7. doi: 10.1021/bi00712a009, 1974.

(Continued)

*Primary Examiner* — J. Christopher Ball
(74) *Attorney, Agent, or Firm* — Dierker & Kavanaugh, P.C.

(57) ABSTRACT

An example of a nanopore sensor device includes one or more cis wells; a cis electrode; a plurality of trans wells, each of the plurality of trans wells separated from the one or more cis wells by a lipid/solid-state membrane having a nanopore; a plurality of trans electrodes, each of the plurality of trans electrodes associated with one of the plurality of trans wells; a first concentration of an electrolyte within the one or more cis wells; and a second concentration of the electrolyte within the trans wells, wherein the first concentration is higher than the second concentration.

23 Claims, 13 Drawing Sheets

(51) Int. Cl.
  *B82B 3/00* (2006.01)
  *C12Q 1/6869* (2018.01)

(56) References Cited

U.S. PATENT DOCUMENTS

| | | | |
|---|---|---|---|
| 7,939,249 | B2 | 5/2011 | Parthasarathy et al. |
| 8,324,360 | B2 | 12/2012 | Kokoris et al. |
| 8,349,565 | B2 | 1/2013 | Kokoris et al. |
| 8,586,301 | B2 | 11/2013 | Kokoris et al. |
| 8,592,182 | B2 | 11/2013 | Kokoris et al. |
| 9,429,561 | B2 | 8/2016 | Burrows et al. |
| 9,670,526 | B2 | 6/2017 | Kokoris et al. |
| 9,708,655 | B2 | 7/2017 | Mandell et al. |
| 9,771,614 | B2 | 9/2017 | Kokoris et al. |
| 9,920,386 | B2 | 3/2018 | Kokoris et al. |
| 10,301,345 | B2 | 5/2019 | Kokoris et al. |
| 10,457,979 | B2 | 10/2019 | Mcruer et al. |
| 10,676,782 | B2 | 6/2020 | Mcruer et al. |
| 10,745,685 | B2 | 8/2020 | Kokoris et al. |
| 10,774,105 | B2 | 9/2020 | Kokoris et al. |
| 10,851,405 | B2 | 12/2020 | Kokoris et al. |
| 10,866,230 | B2 | 12/2020 | Grinstaff et al. |
| 2010/0025238 | A1 | 2/2010 | Gottlieb et al. |
| 2010/0035260 | A1 | 2/2010 | Olasagasti et al. |
| 2010/0072080 | A1 | 3/2010 | Karhanek et al. |
| 2010/0099198 | A1 | 4/2010 | Zhao et al. |
| 2014/0021047 | A1 | 1/2014 | Shim et al. |
| 2014/0190833 | A1 | 7/2014 | Lieber et al. |
| 2015/0111759 | A1 | 4/2015 | Ju et al. |
| 2015/0185200 | A1 | 7/2015 | Burrows et al. |
| 2015/0219593 | A1 | 8/2015 | Kawai et al. |
| 2015/0265994 | A1 | 9/2015 | Hyde et al. |
| 2017/0058336 | A1 | 3/2017 | Ivankin et al. |
| 2017/0168040 | A1 | 6/2017 | Turner et al. |
| 2017/0369944 | A1 | 12/2017 | Barrall et al. |
| 2018/0364214 | A1 | 12/2018 | Maglia et al. |
| 2020/0132664 | A1 | 4/2020 | Boyanov et al. |
| 2021/0263011 | A1 | 8/2021 | Meller et al. |

FOREIGN PATENT DOCUMENTS

| | | |
|---|---|---|
| CN | 104583767 B | 4/2015 |
| EA | 022475 B | 1/2016 |
| EP | 2344891 B1 | 3/2016 |
| JP | 2015521030 A1 | 7/2015 |
| JP | 2016127851 A1 | 7/2016 |
| RU | 2014149813 A1 | 7/2016 |
| WO | 2005105272 A1 | 11/2005 |
| WO | 2011130312 A1 | 10/2011 |
| WO | 2012138357 A1 | 10/2012 |
| WO | 2013153359 A1 | 10/2013 |
| WO | 2014022365 A1 | 2/2014 |
| WO | 2016059417 A1 | 4/2016 |
| WO | 2016187519 A1 | 11/2016 |
| WO | 2016196755 A1 | 12/2016 |
| WO | 2017184866 A1 | 10/2017 |
| WO | 2018236906 A2 | 12/2018 |
| WO | 2019160925 A1 | 8/2019 |
| WO | 2020068400 A2 | 4/2020 |
| WO | 2020247472 A1 | 12/2020 |

OTHER PUBLICATIONS

Arnaud-Neu et al., "Cation Complexation by Chemically Modified Calixarenes. Part 7. Transport of Alkali Cations by p-tert-Butylcalix[n]arene Esters and Amides", J. Chem. Soc., Perkin Trans. 2., 1995, pp. 113-118, 1995.

Bezrukov et al., "Field-Dependent Effect of Crown Ether (18-Crown-6) on Ionic Conductance of a-Hemolysin Channels", Biophysical Journal, vol. 87, Nov. 2004, 3162-3171, 2004.

Geiss et al., "The Protein-Tethered Lipid Bilayer: A Novel Mimic of the Biological Membrane", Biophysical Journal, vol. 87, Nov. 2004, 3213-3220, 2004.

Heins et al., "Effect of Crown Ether on Ion Currents through Synthetic Membranes Containing a Single Conically Shaped Nanopore", J. Phys. Chem. B 2005, 109, 18400-18407, 2005.

Maglia et al., "Enhanced translocation of single DNA molecules through alpha-hemolysin nanopores by manipulation of internal charge", Proceedings of the National Academy of Sciences, National Academy of Sciences, vol. 105, No. 50, Dec. 16, 2008 (Dec. 16, 2008), pp. 19720-19725, DOI: 1O .1073/PNAS.0808296105, 2008.

Bard, "Investigation of Ion-Peptide Interactions Using a Biocompatible Nanopore Probe", Thesis Submitted to the Office of Graduate Studies of Texas A & M University, May 2012, https://oaktrust.library.tamu.edu/handle/1969.1/ETD-TAMU-2012-05-10852, 2012.

Guo, W., et al., "Asymmetric Ion Transport through Ion-Channel-Mimetic Solid-State Nanopores", Accounts of Chemical Research, vol. 46, No. 12, pp. 2834-2846, 2013.

Lin, X. H., et al., "Poisson-Fokker-Planck model for biomolecules translocation through nanopore driven by electroosmotic flow", Science China, vol. 57, No. 11, pp. 2104-2113, 2014.

Hsiao, Pai-Yi, "Polyelectrolyte Threading through a Nanopore", Polymers 2016, vol. 8, Article No. 73, pp. 1-20, doi:10.3390/polym8030073, 2016.

ISA, "International Search Report and Written Opinion for International Application No. PCT/US2018/038337", 14 pages, Jan. 21, 2019.

Qi et al., "Synergic Effects of the Nanopore Size and Surface Charge on the Ion Selectivity of Graphene Membranes", The Journal of Physical Chemistry C, vol. 125, No. 1, Dec. 29, 2020 (Dec. 29, 2020), pp. 507-514, DOI: 10.1021/acs.jpcc.0c09130, 2020.

Butler et al., "Single-molecule DNA detection with an engineered MspA protein nanopore", PNAS, Dec. 30, 2008, vol. 105, No. 52, 20647-20652, https://doi.org/10.1073/pnas.080751410, 2008.

Derrington et al., "Nanopore DNA Sequencing with MspA", PNAS, Sep. 14, 2010, vol. 107, No. 37, 16060-16065, https://www.pnas.org/doi/full/10.1073/pnas.1001831107, 2010.

Besanceney-Webler et al., "Increasing the Efficacy of Bioorthogonal Click Reactions for Bioconjugation: A Comparative Study", Angew. Chem. Int. Ed. 2011, 50, 8051-8056, 2011.

Besanceney-Webler et al., "Increasing the Efficacy of Bioorthogonal Click Reactions for Bioconjugation: A Comparative Study, Supporting Information", anie_201101817_sm_miscellaneous_information.pdf, 19 pages, 2011.

Li et al., "Copper-Free Sonogashira Cross-Coupling For Functionalization of Alkyne-Encoded Proteins in Aqueous Medium and in Bacterial Cells", J. Am. Chem. Soc., Sep. 8, 2011, 133(39): pp. 15316-15319, DOI: 10.1021/ja2066913, 2011.

Wang et al., "Single-molecule DNA detection using a novel SP1 protein nanopore", Chem. Commun., 2013, 49, 1741-1743, 2013.

Wang et al., "Single-molecule DNA detection using a novel SP1 protein nanopore, Supporting Information", https://www.rsc.org/suppdata/cc/c3/c3cc38939a/c3cc38939a.pdf, 5 pages, 2013.

Spicer et al., "Selective Chemical Protein Modification", Nature Communications, 5(4740), pp. 1-14, Published Sep. 5, 2014, DOI: 10.1038/ncomms5740, 2014.

Cohen et al., "An Umpolung Approach for the Chemoselective Arylation of Selenocysteine in Unprotected Peptides", J. Am. Chem. Soc., Jul. 30, 2015, 137(31): pp. 9784-9787, DOI: 10.1021/jacs.5b05447, 2015.

Krall et al., "Site-Selective Protein-Modification Chemistry For Basic Biology and Drug Development", Nature Chemistry, 8(2), Published online Nov. 30, 2015, 11 pages, DOI: 10.1038/NCHEM.2393, 2015.

Vinogradova et al., "Organometallic Palladium Reagents For Cysteine Bioconjugation", Nature, Oct. 29, 2015, 526(7575), pp. 687-691, www.nature.com/doifinder/10.1038/nature15739, 2015.

Cao et al., "Discrimination of Oligonucleotides of Different Lengths With a Wild-Type Aerolysin Nanopore", Nature Nanotechnology, 11: 713-718, Published online Apr. 25, 2016. DOI: 10.1038/NNANO.2016.66, 2016.

Cao et al., "Discrimination of Oligonucleotides of Different Lengths With a Wild-Type Aerolysin Nanopore, Supplementary Information", https://static-content.springer.com/esm/art%3A10.1038%2Fnnano.2016.66/MediaObjects/41565_2016_BFnnano201666_MOESM11_ESM.pdf, 30 pages, 2016.

(56)                    References Cited

OTHER PUBLICATIONS

Wloka et al., "Alpha-Helical Fragaceatoxin C Nanopore Engineered For Double-Stranded and Single-Stranded Nucleic Acid Analysis", Angew. Chem. Int. Ed. 2016, 55(40), 12494-12498, DOI: 10.1002/ange.201606742, 2016.

Cheng et al., "Synthesis of a Novel Fluorescent Ruthenium Complex By an Appended Ac4glcnac Moiety By Click Reaction", Molecules (2018) 23(7), 1649; doi:10.3390/molecules23071649, 10 pages, 2018.

Griffiths et al., "Site-Selective Modification of Peptides and Proteins via Interception of Free-Radical-Mediated Dechalcogenation", Angew. Chem. Int. Ed. 2020, 59(52), pp. 23659-23667, 2020.

Sato et al., "Site-Selective Protein Chemical Modification of Exposed Tyrosine Residues Using Tyrosine Click Reaction", Bioconjugate Chem. 2020, 31(5), pp. 1417-1424, 2020.

Sato et al., "Site-Selective Protein Chemical Modification of Exposed Tyrosine Residues Using Tyrosine Click Reaction, Supporting Information", https://pubs.acs.org/doi/suppl/10.1021/acs.bioconjchem.0c00120/suppl_file/bc0c00120_si_001.pdf, 32 pages, 2020.

Van Der Verren et al., "A Dual-Constriction Biological Nanopore Resolves Homonucleotide Sequences With High Fidelity", Nature Biotechnology, Jul. 6, 2020, 38(12), pp. 1415-1420, https://doi.org/10.1038/s41587-020-0570-8, 2020.

Vantourout et al., "Serine-Selective Bioconjugation", J. Am. Chem. Soc. 2020, 142(41), 17236-17242, https://dx.doi.org/10.1021/jacs.0c05595, 2020.

ISA, "International Search Report and Written Opinion for International Application No. PCT/US2022/018371", dated May 23, 2022, 12 pages, 2022.

ISA, "International Search Report and Written Opinion for International Application No. PCT/US2022/019802", dated Jun. 21, 2022, 12 pages, 2022.

Tay et al., "Targeted Activation in Localized Protein Environments via Deep Red Photoredox Catalysis", Nature Chemistry, Jan. 15, 2023, 101-109, Published online Oct. 10, 2022, doi.org/10.1038/s41557-022-01057-1, 2022.

An et al., "Crown ether-electrolyte interactions permit nanopore detection of individual DNA abasic sites in single molecules", Proceedings of the National Academy of Sciences, vol. 109, No. 29, Jul. 17, 2012 (Jun. 18, 2012), pp. 11504-11509, DOI: 10.1073/pnas.1201669109, Jul. 17, 2012.

Jou et al., "Effects of Nanopore Charge Decorations on the Translocation Dynamics of DNA", Biophysical Journal, vol. 113, No. 8, Oct. 17, 2017 (Oct. 17, 2017), pp. 1664-1672. DOI:10.1016/j.bpj.2017.08.045 , Oct. 17, 2017.

Astier et al., "Toward single molecule DNA sequencing: direct identification of ribonucleoside and deoxyribonucleoside 5'-monophosphates by using an engineered protein nanopore equipped with a molecular adapter", J. Am. Chem. Soc. Feb. 8, 2006, 128(5), pp. 1705-1710, 2006.

Borsley et al., "In Situ Synthetic Functionalization of a Transmembrane Protein Nanopore", ACS Nano. Jan. 23, 2018, 12(1), pp. 786-794. doi: 10.1021/acsnano.7b08105. Epub 2017 Dec. 19, 2017.

Haugland et al., "Synthetically Diversified Protein Nanopores: Resolving Click Reaction Mechanisms", ACS Nano. Apr. 23, 2019, 13(4), pp. 4101-4110. doi: 10.1021/acsnano.8b08691. Epub 2019 Mar. 18, 2019.

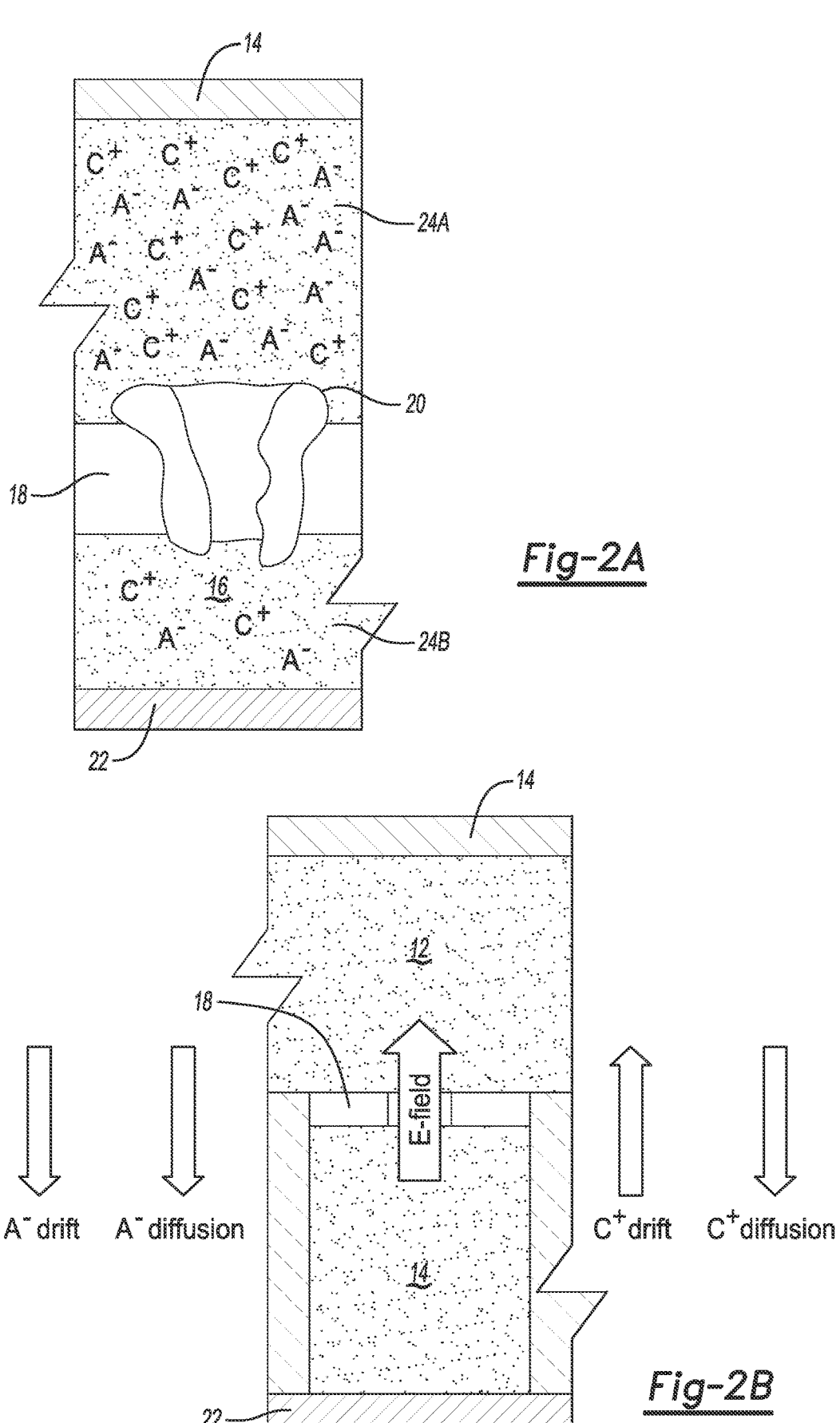
_Fig-2A_
_Fig-2B_

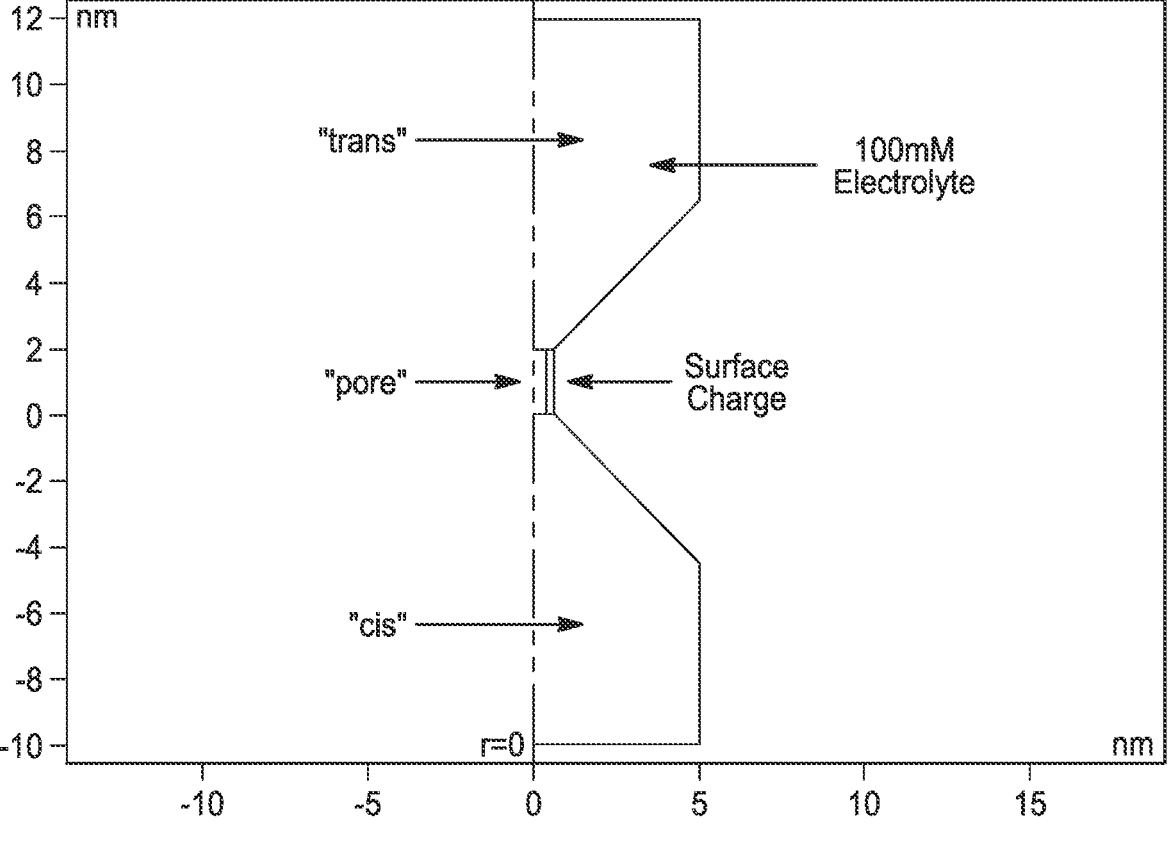
<u>*Fig-8*</u>

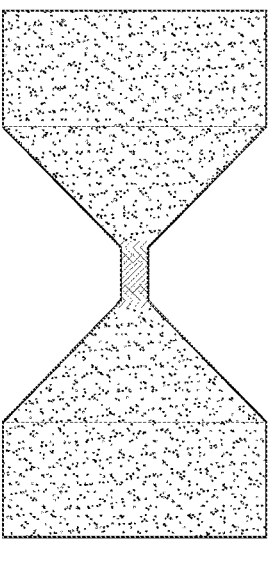
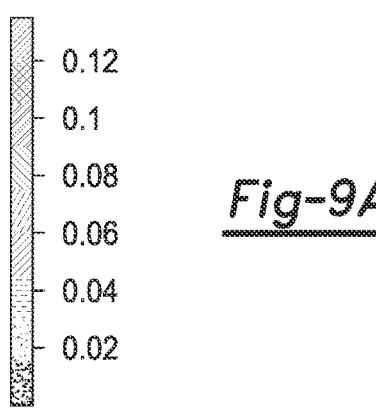
*Fig-9A*
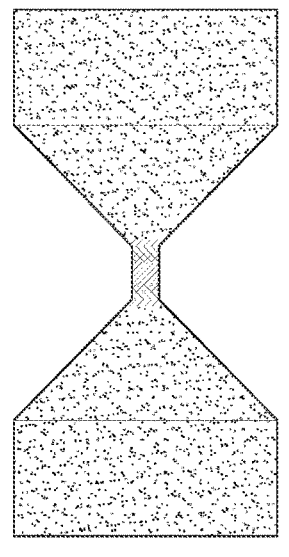
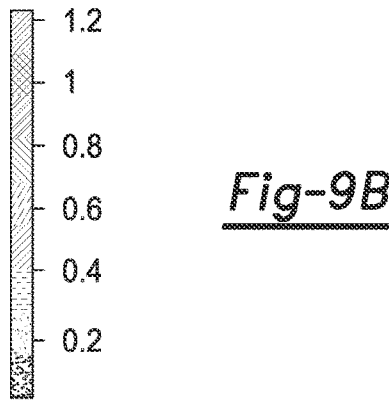
*Fig-9B*
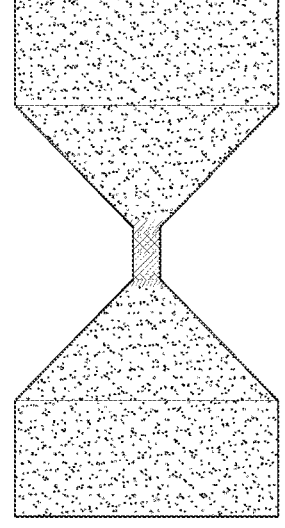
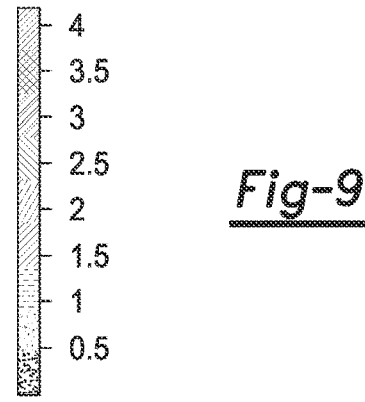
*Fig-9C*

NANOPORE SENSOR DEVICES

CROSS-REFERENCE TO RELATED APPLICATION

This application claims the benefit of U.S. Provisional Application Ser. No. 63/168,646, filed Mar. 31, 2021, the contents of which is incorporated by reference herein in its entirety.

BACKGROUND

Various polynucleotide sequencing techniques involve performing a large number of controlled reactions on local support surfaces or within predefined reaction chambers. The designated reactions may then be observed or detected, and subsequent analysis may help identify or reveal properties of the polynucleotide involved in the reaction. Another polynucleotide sequencing technique has been developed that utilizes a nanopore, which can provide a channel for an ionic electrical current. A polynucleotide or label/tab of an incorporated nucleotide is driven into the nanopore, changing the resistivity of the nanopore. Each nucleotide (or series of nucleotides) or each label/tab (or series of labels/tags) yields a characteristic electrical signal, and the record of the signal levels corresponds to the sequence of the polynucleotide. In prior nanopore sensor devices (at t=0), the current is equally carried by the electrolyte translocating through the nanopore in opposite directions between a cis well and a trans well. However, such nanopore sequencing devices suffer from low lifetimes.

SUMMARY

In a first example, a nanopore sensor device comprises one or more cis wells; a cis electrode; a plurality of trans wells, each of the plurality of trans wells separated from the one or more cis wells by a lipid/polymer/solid-state membrane having a nanopore; a plurality of trans electrodes, each of the plurality of trans electrodes associated with one of the plurality of trans wells; a first concentration of an electrolyte within the one or more cis wells; and a second concentration of the electrolyte within the trans wells, wherein the first concentration is higher than the second concentration.

In a second example, a nanopore sensor kit comprises i) a nanopore sensor device, including: one or more cis wells including a fluid inlet; a cis electrode; a plurality of trans wells, each of the plurality of trans wells separated from the one or more cis wells by a lipid/polymer/solid-state membrane having a nanopore; a plurality of trans electrodes, each of the plurality of trans electrodes associated with one of the plurality of trans wells; and a first concentration of an electrolyte within the one or more cis wells and the plurality of trans well; and ii) a second concentration of the electrolyte to be introduced into the one or more cis wells through the fluid inlet such that the one or more cis wells contain the second concentration of the electrolyte and the plurality of trans wells contain the first concentration of the electrolyte at an initial cycle of the nanopore sensor device, wherein the second concentration is higher than the first concentration.

In a third example, a method of detecting an ionic current to analyze a biological compound comprises providing a nanopore within a membrane separating a cis well and a trans well, the nanopore having a plurality of positively charged residues on an inner surface of the nanopore; providing an electrolyte within the cis well and the trans well; and applying an electric current between a cis cathode at least partially exposed to the cis well and a trans anode at least partially exposed to the trans well to generate an ionic current through the nanopore, wherein the plurality of positively charged residues of the nanopore inhibits translocation of cations from the trans well to the cis well during application of the electric current.

In a fourth example, a nanopore sensor device comprises one or more cis wells; a cis electrode; a plurality of trans wells, each of the plurality of trans wells separated from the one or more cis wells by a lipid/polymer/solid-state membrane having a nanopore; a plurality of trans electrodes, each of the plurality of trans electrodes associated with one of the plurality of trans wells; an electrolyte solution including a redox-inactive buffer that includes anions having a diameter greater than a diameter of a constriction zone of the nanopore and a redox species.

It is to be understood that any features of the any of the examples set forth herein may be combined together in any desirable manner. For example, any combination of features of the first example and/or of the second example and/or of the third example and/or of the fourth example may be used together, and/or may be combined with any of the other examples disclosed herein to achieve the benefits as described in this disclosure, including, for example, controlling the depletion of an electrolyte species.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 2A is an enlarged and schematic view of a portion of the nanopore sensor device, where the cis well includes a higher concentration of the electrolyte species in than the trans well;

FIG. 2B is a schematic illustration of the ionic species drift and diffusion currents for the example of the nanopore sensor device where the cis well includes a higher concentration of the electrolyte species in than the trans well;

FIG. 8 is an illustration of the COSMOL simulation domain used in Example 4;

FIGS. 9A through 9C depict the 3D finite element analysis results, showing the computed spatial distribution (log scale) of the Cl:K ratio in the simulation domain;

DETAILED DESCRIPTION

Figure 1:
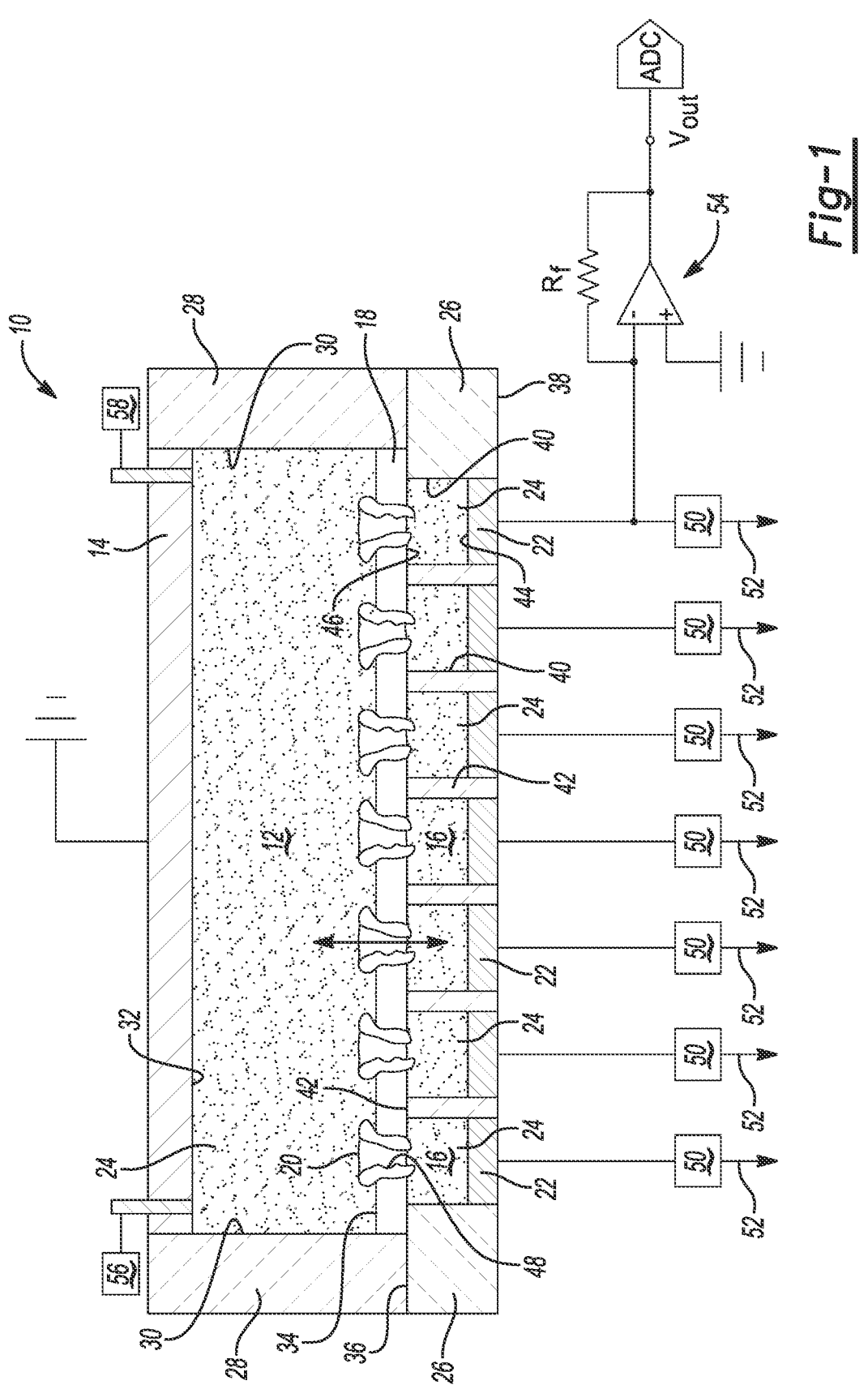
FIG. 1 is a schematic and partially cross-sectional view of an example of a nanopore sensor device disclosed herein.

The technique of nanopore sequencing uses variations in electrical signal to distinguish nucleotide bases. Nanopore sensor devices include a cis well, a cis electrode, a plurality of trans wells, and a trans electrode associated with each of the plurality of trans wells. Each trans well is separated from the cis well by a lipid/polymer/solid-state membrane having a nanopore. As such, each trans well is also associated with a respective nanopore. Faradaic current between the cis electrode and trans electrode is established by redox species with or without an electrolyte buffer.

In certain examples, the electrodes are active (i.e., the electrodes actively participate in the redox reaction), and the reactive electrolyte species (i.e., redox anions) are consumed by being plated out at the trans electrode in a positive polarity to support Faradaic current through the system. In certain examples, the electrodes are passive (i.e., the electrodes do not actively participate in the redox reaction) and the reactive electrolyte species (i.e., redox couple ions) are consumed by being oxidized at the trans electrode in a positive polarity to support Faradaic current through the system. In these examples, the redox couple is suspended in a redox-inactive electrolyte buffer.

The trans electrode is located in a confined compartment with a limited volume and thus, in these instances, the replenishment of the reactive electrolyte species in the trans well is dependent upon the transport of the species through the nanopore from the cis well. In prior nanopore sensor devices, the concentration of reactive electrolyte within the trans well may become partially depleted, which reduces the operability of the nanopore sensor device.

In an example of an Ag/Cl redox system with active electrodes, chloride anions may be partially depleted on the trans side due to plating out onto the trans electrode and may not be fully replaced by transport of chloride anions through the nanopore. For example, when two chloride ions are consumed by plating out at the trans electrode, one chloride ion transits through the pore into the trans well. If the concentration of chloride ions is low in the trans well, there is reduced reactive electrolyte species in the trans well. This reduces the ability to carry ionic current, and thus results in reduced signal level and detection by the nanopore sensor device.

Because the reactive electrolyte species is replenished at a fraction of how much is plated out in prior nanopore sensor devices, depletion or partial consumption of the electrochemically active electrolyte species in the trans well occurs over time. The partial consumption of the reactive electrolyte species depends on several factors, including the current that passes through the nanopore, and the size of the trans well (e.g., larger wells are generally associated with less reagent consumption and smaller chambers are generally associated with more reagent consumption). The time to complete depletion of the reactive electrolyte species in the trans well of prior nanopore sensor devices can be estimated from equation 1:

$$t_{max} \sim 2\frac{VCN_A}{1000}\frac{q}{i} \qquad \text{(equation 1)}$$

where V (cm$^3$) is the trans well volume, C (mol/L) is the reactive electrolyte species concentration at t=0 in the trans well, $N_A$ is Avogadro's number, q (Coulomb or C) is the elementary charge of the reactive electrolyte species, and i (A) is the nanopore current.

In prior nanopore sensor devices, partial consumption may be evidenced by a reduction in the initial reagent concentration, where the reduction is greater than a factor of 10. In some instances, the reduction ranges from a factor of 20 to a factor of 100. For example, the chloride concentration of an electrolyte solution having an initial chloride concentration of about 300 mM in a 10 μm trans well can be depleted to about 10 mM, and thus the initial concentration is reduced by a factor of about 30. For another example, the chloride concentration of an electrolyte solution having an initial chloride concentration of about 10 mM in a 10 μm trans well can be depleted to about 0.1 mM, and thus the initial concentration is reduced by a factor of about 100. It is to be understood that the partial consumption/depletion can approach 100% (i.e., the partially consumed electrolyte species remaining in the system approaches 0%), but an equilibrium will establish between the electrolyte anions and cations, even at such low levels of the partially consumed species.

In an example of an ferrocyanide/ferricyanide redox couple in an electrolyte buffer with passive electrodes, ferrocyanide ions (e.g., $Fe(CN)_6^{4-}$) are oxidized to ferricyanide ions (e.g., $Fe(CN)_6^{3-}$) at the trans electrode in a forward polarity. The reactive electrolyte species may be partially depleted on the trans side due to being consumed at the trans electrode and may not be fully replaced by transport of reactive electrolyte species through the nanopore.

Certain embodiments of the nanopore sensor device and method disclosed herein reduce the depletion of the reactive electrolyte species at the trans well(s) of the nanopore sensor device. In these examples, a reduction in the initial reactive electrolyte species concentration at the trans well(s) may still occur; however, the reduction is less than 10% and likely less than 1%. As such, more of the reactive electrolyte species is present over time (e.g., compared to the prior nanopore sensor devices provided above), and thus depletion of the reactive electrolyte species is reduced. In certain examples, depletion of the reactive electrolyte species is reduced by inhibiting the transport of redox cations, buffer anions or both through the nanopore(s) of the nanopore sensor device. In these certain examples, the reduction of the transport of the redox cations is accomplished using unbalanced electrolyte concentrations, modified nanopores, and/ or charge induced in the nanopores. In these certain examples, the reduction of the transport of buffer anions is accomplished using unbalanced electrolyte concentrations and/or utilizing a bulky buffer anion. Reducing the transport of the redox cations and/or buffer anions through the nanopore results in a higher amount of the ionic charge to be carried by the reactive electrolyte species. Thus, an increased amount of reactive electrolyte species is transported into the trans well from the cis well. As a result, reactive electrolyte species depletion from trans well(s) of the nanopore sensor device is reduced and the lifetime of the nanopore sensor device is extended.

As mentioned above, the technique of nanopore sequencing uses variations in electrical signal to distinguish nucleotide bases. A depletion in the reactive electrolyte species in the trans wells reduces ionic current and lowers the signal detected by the nanopore sensor device. By increasing the replenishment of reactive electrolyte species from the cis well into the trans well, the lifetime of the nanopore sensor device may be increased.

Definitions

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the nanopore sensor device and/or the various components of the nanopore sensor device. It is to be understood that these directional terms are not meant to imply a specific orientation, but are used to designate relative orientation between components. The use of directional terms should not be interpreted to limit the examples disclosed herein to any specific orientation(s).

The terms first, second, etc. also are not meant to imply a specific orientation or order, but rather are used to distinguish one component from another.

It is to be understood that the ranges provided herein include the stated range and any value or sub-range within the stated range, as if such values or sub-ranges were explicitly recited. For example, a range from about 50 mM to about 500 mM should be interpreted to include not only the explicitly recited limits of from about 50 mM to about 500 mM, but also to include individual values, such as about 100 mM about 335 mM, about 400.5 mM, about 490 mM, etc., and sub-ranges, such as from about 75 mM to about 475 mM, from about 200 mM to about 300 mM, etc. Furthermore, when "about" and/or "substantially" are/is utilized to describe a value, this is meant to encompass minor variations (up to +/−10%) from the stated value.

As used herein, the terms "fluidically connecting," "fluid communication," "fluidically coupled," and the like refer to two spatial regions being connected together such that a liquid or gas may flow between the two spatial regions. For example, a cis well may be fluidically connected to a trans well or a plurality of trans wells, such that at least a portion of an electrolyte solution may transit between the connected wells. The two spatial regions may be in fluid communication through a nanopore, or through one or more valves, restrictors, or other fluidic components that are to control or regulate a transit of ions through a system.

As used herein, the term "interstitial region" refers to an area in a substrate/solid support or a membrane, or an area on a surface that separates other areas, regions, features associated with the support or membrane or surface. For example, an interstitial region of a membrane can separate one nanopore of an array from another nanopore of the array. For another example, an interstitial region of a substrate can separate one trans well from another trans well. The two areas that are separated from each other can be discrete, i.e., lacking physical contact with each other. In many examples, the interstitial region is continuous whereas the areas are discrete, for example, as is the case for a plurality of nanopores defined in an otherwise continuous membrane, or for a plurality of wells defined in an otherwise continuous support. The separation provided by an interstitial region can be partial or full separation. Interstitial regions may have a surface material that differs from the surface material of the features defined in the surface. For example, the surface material at the interstitial regions may be a lipid material, and a nanopore formed in the lipid material can have an amount or concentration of polypeptide that exceeds the amount or concentration present at the interstitial regions. In some examples, the polypeptide may not be present at the interstitial regions.

As used herein, the term "membrane" refers to a non-permeable or semi-permeable barrier or other sheet that separates two liquid/gel chambers (e.g., a cis well and a trans well) which can contain the same compositions or different compositions therein. The permeability of the membrane to any given species depends upon the nature of the membrane. In some examples, the membrane may be non-permeable to ions, to electric current, and/or to fluids. For example, a lipid membrane may be impermeable to ions (i.e., does not allow any ion transport therethrough), but may be at least partially permeable to water (e.g., water diffusivity ranges from about 40 μm/s to about 100 μm/s). For another example, a synthetic/solid state membrane, such as silicon nitride, may be impermeable to ions, electric charge, and fluids (i.e., the diffusion of all of these species is zero). Any membrane may be used in accordance with the present disclosure, so long as the membrane can include a transmembrane nanoscale opening (e.g., a nanopore) and can maintain a potential difference across the membrane. The membrane may be a monolayer or a multilayer membrane. A multilayer membrane includes two or more layers, each of which is a non-permeable or semi-permeable material.

The membrane may be formed of materials of biological or non-biological origin. A material that is of biological origin refers to material derived from or isolated from a biological environment such as an organism or cell, or a synthetically manufactured version of a biologically available structure (e.g., a biomimetic material).

An example membrane that is made from the material of biological origin includes a monolayer formed by a bola-lipid. Another example membrane that is made from the material of biological origin includes a lipid bilayer. Suitable lipid bilayers include, for example, a membrane of a cell, a membrane of an organelle, a liposome, a planar lipid bilayer, and a supported lipid bilayer. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by a method in which a lipid monolayer is carried on an aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has at least partially evaporated, the solution/air interfaces on either side of the aperture are physically moved up and down past the aperture until a bilayer is formed. Other suitable methods of bilayer formation include tip-dipping, painting bilayers, and patch-clamping of liposome bilayers. Any other methods for obtaining or generating lipid bilayers may also be used.

A material that is not of biological origin may also be used as the membrane. Some of these materials are solid state materials and can form a solid state membrane, and others of these materials can form a thin liquid film or membrane. The solid state membrane can be a monolayer, such as a coating or film on a supporting substrate (i.e., a solid support), or can be a free-standing element. The solid state membrane can also be a composite of multilayered materials in a sandwich configuration. Any material not of biological origin may be used, as long as the resulting membrane can include a transmembrane nanoscale opening and can maintain a potential difference across the membrane. The membranes may include organic materials, inorganic materials, or both. Examples of suitable solid state materials include, for example, microelectronic materials, insulating materials (e.g., silicon nitride ($Si_3N_4$), aluminum oxide ($Al_2O_3$), hafnium oxide ($HfO_2$), tantalum pentoxide ($Ta_2O_5$), silicon oxide ($SiO_2$), etc.), some organic and inorganic polymers (e.g., polyamide, plastics, such as polytetrafluoroethylene (PTFE), or elastomers, such as two-component addition-cure silicone rubber), and glasses. In addition, the solid state membrane can be made from a monolayer of graphene, which is an atomically thin sheet of carbon atoms densely packed into a two-dimensional honeycomb lattice, a multilayer of graphene, or one or more layers of graphene mixed with one or more layers of other solid state materials. A graphene-containing solid state membrane can include at least one graphene layer that is a graphene nanoribbon or graphene nanogap, which can be used as an electrical sensor to characterize the target polynucleotide. The solid state membrane can be made by any suitable method. As examples, the graphene membrane can be prepared through either chemical vapor deposition (CVD) or exfoliation from graphite. Examples of suitable thin liquid film materials that may be used include diblock copolymers, triblock copolymers, such as amphiphilic PMOXA-PDMS-PMOXA ABA triblock copolymers.

As used herein, the term "nanopore" is intended to mean a hollow structure discrete from and extending across the membrane that permits ions, electric current, and/or fluids to cross from one side of the membrane to the other side of the membrane. For example, a membrane that inhibits the passage of ions or water soluble molecules can include a nanopore structure that extends across the membrane to permit the passage (through a nanoscale opening/channel extending through the nanopore structure) of the ions or water soluble molecules from one side of the membrane to the other side of the membrane. The diameter of the nanoscale opening/channel can vary along its length (i.e., from one side of the membrane to the other side of the membrane), but at any point is on the nanoscale (i.e., from about 1 nm to about 100 nm, or to less than 1000 nm). Examples of the nanopore include, for example, biological nanopores, solid state nanopores, and biological and solid state hybrid nanopores.

As used herein, the term "diameter" is intended to mean a longest straight line inscribable in a cross-section of a nanoscale opening through a centroid of the cross-section of the nanoscale opening. It is to be understood that the nanoscale opening may or may not have a circular or substantially circular cross-section (the cross-section of the nanoscale opening being substantially parallel with the cis/trans electrodes). Further, the cross-section may be regularly or irregularly shaped.

As used herein, the term "biological nanopore" is intended to mean a nanopore whose structure portion is made from materials of biological origin. Biological origin refers to a material derived from or isolated from a biological environment such as an organism or cell, or a synthetically manufactured version of a biologically available structure. Biological nanopores include, for example, polypeptide nanopores and polynucleotide nanopores.

As used herein, the term "polypeptide nanopore" is intended to mean a protein/polypeptide that extends across the membrane, and permits ionsand/or fluids to flow therethrough from one side of the membrane to the other side of the membrane. A polypeptide nanopore can be a monomer, a homopolymer, or a heteropolymer. Structures of polypeptide nanopores include, for example, an α-helix bundle nanopore and a β-barrel nanopore. Example polypeptide nanopores include α-hemolysin, *Mycobacterium smegmatis* porin A (MspA), gramicidin A, maltoporin, OmpF, OmpC, PhoE, Tsx, F-pilus, etc. The protein α-hemolysin is found naturally in cell membranes, where it acts as a channel for ions or molecules to be transported in and out of cells. *Mycobacterium smegmatis* porin A (MspA) is a membrane porin produced by Mycobacteria, which allows hydrophilic molecules to enter the bacterium. MspA forms a tightly interconnected octamer and transmembrane beta-barrel that resembles a goblet and contains a central channel/pore.

A polypeptide nanopore can be synthetic. A synthetic polypeptide nanopore includes a protein-like amino acid sequence that does not occur in nature. The protein-like amino acid sequence may include some of the amino acids that are known to exist but do not form the basis of proteins (i.e., non-proteinogenic amino acids). The protein-like amino acid sequence may be artificially synthesized rather than expressed in an organism and then purified/isolated.

As used herein, the term "polynucleotide nanopore" is intended to include a polynucleotide that extends across the membrane, and permits ions and/or fluids to flow from one side of the membrane to the other side of the membrane. A polynucleotide pore can include, for example, a polynucleotide origami (e.g., nanoscale folding of DNA to create the nanopore).

Also as used herein, the term "solid state nanopore" is intended to mean a nanopore whose structure portion includes materials of non-biological origin (i.e., not of biological origin). A solid-state nanopore can be formed of an inorganic or organic material. Solid state nanopores include, for example, silicon nitride nanopores, silicon dioxide ($SiO_2$) nanopores, and graphene nanopores.

The nanopores disclosed herein may be hybrid nanopores. A "hybrid nanopore" refers to a nanopore including materials of both biological and non-biological origins. An example of a hybrid nanopore includes a polypeptide-solid state hybrid nanopore and a polynucleotide-solid state nanopore.

As used herein, the term "nanopore sensor device" or "nanopore sequencer" refers to any of the devices disclosed herein that can be used for nanopore sequencing. In the examples disclosed herein, during nanopore sequencing, the nanopore is immersed in example(s) of the electrolyte disclosed herein and a potential difference is applied across the membrane. In an example, the potential difference is an electric potential difference or an electrochemical potential difference. An electrical potential difference can be imposed across the membrane via a voltage source that injects or administers current to at least one of the ions of the electrolyte contained in the cis well or one or more of the trans wells. An electrochemical potential difference can be established by a difference in ionic composition of the cis and trans wells in combination with an electrical potential. The different ionic composition can be, for example, different ions in each well or different concentrations of the same ions in each well.

The application of the potential difference across the nanopores may force the translocation of a nucleic acid through the nanopore. One or more signals are generated that correspond to the translocation of the nucleotide through the nanopore. Accordingly, as a target polynucleotide, or as a mononucleotide or a probe derived from the target polynucleotide or mononucleotide, transits through the nanopore, the current across the membrane changes due to base-dependent (or probe dependent) blockage of the constriction, for example. The signal from that change in current can be measured using any of a variety of methods. Each signal is unique to the species of nucleotide(s) (or probe) in the nanopore, such that the resultant signal can be used to determine a characteristic of the polynucleotide. For example, the identity of one or more species of nucleotide(s) (or probe) that produces a characteristic signal can be determined.

As used herein, a "nucleotide" includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The phosphate groups may be in the mono-, di-, or tri-phosphate form. These nucleotides are natural nucleotides, but it is to be further understood that non-natural nucleotides, modified nucleotides or analogs of the aforementioned nucleotides can also be used.

As used herein, the term "signal" is intended to mean an indicator that represents information. Signals include, for example, an electrical signal and an optical signal. The term "electrical signal" refers to an indicator of an electrical quality that represents information. The indicator can be, for example, current, voltage, tunneling, resistance, potential, conductance, capacitance, frequency, or other changes in an electrical waveform.

The term "substrate" refers to a rigid, solid support that is insoluble in aqueous liquid and is incapable of passing a liquid absent an aperture, port, or other like liquid conduit. In the examples disclosed herein, the substrate may have wells or chambers defined therein. Examples of suitable substrates include glass and modified or functionalized glass, plastics (including acrylics, polystyrene and copolymers of styrene and other materials, polypropylene, polyethylene, polybutylene, polyurethanes, polytetrafluoroethylene (PTFE) (such as TEFLON® from Chemours), cyclic olefins/cyclo-olefin polymers (COP) (such as ZEONOR® from Zeon), polyimides, etc.), nylon, ceramics, silica or silica-based materials, silicon and modified silicon, carbon, metals, inorganic glasses, and optical fiber bundles.

A "stimulus source" refers to an electronic device that is to provide a stimulus that causes ionic current to flow through the nanopore. In one example, the stimulus source may be a current source or a voltage source coupled to the cis and/or trans electrodes. In another example, the stimulus source may be any source creating an electric field between the cis well and the trans well.

As used herein, the terms "well", "cavity" and "chamber" are used synonymously, and refer to a discrete feature defined in the device that can contain a fluid (e.g., liquid, gel, gas). A "cis well" is a common chamber that contains or is partially defined by a cis electrode, and is also fluidically connected to each of a plurality of trans wells through a respective nanopore. Examples of an array of the present device may have one cis well or multiple cis wells. Each "trans well" is a single chamber that contains or is partially defined by its own trans electrode, and is also fluidically connected to one cis well. Each trans well is electrically isolated from each other trans well. In some examples, each trans well is connected to a respective stimulus source, and to a respective amplifier (e.g., Axopatch 200B amplifiers) to amplify electrical signals passing through respective nanopores associated with each of the trans wells. In other examples, the trans wells are connected to a single stimulus source which individually addresses the trans wells via multiplexing. Further, it is to be understood that the cross-section of a well taken parallel to a surface of a substrate at least partially defining the well can be curved, square, polygonal, hyperbolic, conical, angular, etc.

The aspects and examples set forth herein and recited in the claims can be understood in view of the above definitions.

Nanopore Sensor Device

Referring now to FIG. 1, an example of a nanopore sensor device 10 is depicted. The nanopore sensor device 10 includes one or more cis wells 12, a cis electrode 14, a plurality of a plurality of trans wells 16, each of the plurality of trans wells 16 separated from the one or more cis wells 12 by a lipid/polymer/solid-state membrane 18 having a nanopore 20; a plurality of trans electrodes 22, each of the plurality of trans electrodes 22 associated with one of the plurality of trans wells 16. The example nanopore sensor device 10 also includes an electrolyte solution 24 in the cis and trans wells 12, 16. Different examples of the device 10 include different examples of the electrolyte solution 24, which will be described in reference to FIG. 2A through FIG. 4.

As shown in FIG. 1, the nanopore sensor device 10 includes a substrate 26. The substrate 26 may include a plurality of trans wells 16 defined therein. Each of the trans wells 16 may be fluidically connected to the common cis well 12 by a respective nanopore 20. While one common cis well 12 is shown in FIG. 1, it is to be understood that the nanopore sensor device 10 may include several cis wells 12 that are fluidically isolated from one another and are fluidically connected to respective sets of trans wells 16 defined in the substrate 26. Multiple cis wells 12 may be desirable, for example, in order to enable the measurement of multiple samples on a single substrate 26.

The fluid communication through the nanopore(s) 20 is indicated by the arrow in FIG. 1. Also, as shown in FIG. 1, the membrane 18 may be positioned on the substrate 26 between the cis well 12 and the trans well(s) 16, and the nanopore(s) 20 may be positioned in, and extend through the membrane 18 to establish the fluidic connection between the cis well 12 and the trans well(s) 16.

The cis well 12 is a fluid chamber that is defined on a portion of the substrate 26 by sidewall(s) 28 that are connected to the substrate 26. In some examples, the sidewall(s) 28 and the substrate 26 may be integrally formed such that they 28, 26 are formed from a continuous piece of material (e.g., glass or plastic). In other examples, the sidewall(s) 28 and the substrate 26 may be separate components that are coupled to each other. In an example, the sidewall(s) 28 are photo patternable polymers.

In the example shown in FIG. 1, the cis well 12 has interior walls 30 that are defined by the sidewall(s) 28, an upper surface 32 that is defined by the cis electrode 14, and a lower surface 34 that is defined by the membrane 18. Thus, the cis well 12 is formed within the space defined by the cis electrode 14, the portion of the substrate 26, and the membrane 18. It is to be understood that the lower surface 34 has opening(s) through the nanopore(s) 20 that are positioned in the membrane 18. The cis well 12 may have any suitable dimensions. In an example, the cis well 12 ranges from about 1 mm×1 mm to about 5 mm×5 mm.

The cis electrode 14, whose interior surface is the upper surface 32 of the cis well 12, may be physically connected to the sidewall(s) 28. The cis electrode 14 may be physically connected to the sidewall(s) 28, for example, by an adhesive or another suitable fastening mechanism. The interface between the cis electrode 14 and the sidewall(s) 28 may seal the upper portion of the cis well 12.

The cis electrode 14 that is used depends, at least in part, upon the electrolyte species in the electrolyte solution 24 (or 24A, 24B, 24C described herein). In some examples, the cis electrode 14 may be an active electrode that takes part in the chemical reaction with an electrochemically active electrolyte species, and can be oxidized or reduced in the half-cell reaction. Examples of active electrodes include silver (Ag), copper (Cu), zinc (Zn), lead (Pb), etc. In other examples, the cis electrode 14 may be an inactive (or inert) electrode that transfers electrons rather than exchange ions with the electrolyte solution 24. Examples of inactive electrodes include platinum (Pt), carbon (C) (e.g., graphite, diamond, etc.), gold (Au), rhodium (Rh), etc. In an example in the nanopore sensor 10 utilizing an electrolyte solution 24 with an electrically active anion (e.g., chloride, Cl$^-$), the cis electrode 14 may be a silver/silver chloride (Ag/AgCl) electrode.

The cis well 12 is capable of maintaining the electrolyte solution 24 in contact with the nanopore(s) 20. In an example, the cis well 12 is in contact with an array of nanopores 20, and thus is capable of maintaining the modified electrode 24 in contact with each of the nanopores 20 in the array.

As illustrated in FIG. 1, the nanopore sensor device 10 includes a plurality of trans wells 16. Each trans well 16 is a fluid chamber that is defined in a portion of the substrate 26. Generally, the trans wells 16 may extend through the thickness of the substrate 26 and may have openings at opposed ends (e.g., a top end 36 and a bottom end 38) of the substrate 26. In the example shown in FIG. 1, each trans well 16 has sidewalls 40 that are defined by the substrate 26 and/or by interstitial regions 42 of the substrate 26, a lower surface 44 that is defined by a trans electrode 22, and an upper surface 46 that is defined by the membrane 18. Thus, each trans well 16 is formed within the space defined by the trans electrode 22, the other portion and/or interstitial regions 42 of the substrate 26, and the membrane 18. It is to be understood that the upper surface 46 has opening(s) through the nanopore(s) 20 positioned in the membrane 18.

The trans electrode 22, whose interior surface is the lower surface 44 of the trans well 16, may be physically connected to the substrate 26 (e.g., to the interstitial regions 42 or to an interior wall of the substrate 26). The trans electrode 22 may be fabricated in the process of forming the substrate 26 (e.g., during the formation of the trans wells 16). Microfabrication techniques that may be used to form the substrate 26 and the trans electrode 22 include lithography, metal deposition and liftoff, dry and/or spin on film deposition, etching, etc. The interface between the trans electrode 22 and the substrate 26 may seal the lower portion of the trans well 16.

The trans electrode 22 that is used depends, at least in part, upon the electrolyte species in the electrolyte solution 24 (or 24A, 24B, 24C described herein). The trans electrode 22 may be an active electrode that takes part in the chemical reaction with an electrochemically active electrolyte species, and can be oxidized or reduced in the half-cell reaction. Any of the examples of the active electrodes set forth herein for the cis electrode 14 may be used as the trans electrode 22. In other examples, the trans electrode 22 may be an inactive (or inert) electrode that transfers electrons rather than exchange ions with the electrolyte solution 24. Any of the examples set forth herein for the cis electrode 14 may be used as the trans electrode 22. In an example in the nanopore sensor 10 utilizing an electrolyte solution 24 with an electrically active anion (e.g., chloride, Cl$^-$), the trans electrode 22 may be a silver/silver chloride (Ag/AgCl) electrode.

Many different layouts of the trans wells 16 may be envisaged, including regular, repeating, and non-regular patterns. In an example, the trans wells 16 are disposed in a hexagonal grid for close packing and improved density. Other layouts may include, for example, rectilinear (i.e., rectangular) layouts, triangular layouts, and so forth. As examples, the layout or pattern can be an x-y format of trans wells 16 that are in rows and columns. In some other examples, the layout or pattern can be a repeating arrangement of trans wells 16 and/or interstitial regions 42. In still other examples, the layout or pattern can be a random arrangement of trans wells 16 and/or interstitial regions 42. The pattern may include spots, posts, stripes, swirls, lines, triangles, rectangles, circles, arcs, checks, plaids, diagonals, arrows, squares, and/or cross-hatches.

The layout may be characterized with respect to the density of the trans wells 16 (i.e., number of trans wells 16 in a defined area of the substrate 26). For example, the trans wells 16 may be present at a density ranging from about 10 wells per mm$^2$ to about 1,000,000 wells per mm$^2$. The density may be tuned to different densities including, for example, a density of at least about 10 per mm$^2$, about 5,000 per mm$^2$, about 10,000 per mm$^2$, about 0.1 million per mm$^2$, or more. Alternatively or additionally, the density may be tuned to be no more than about 1,000,000 wells per mm$^2$, about 0.1 million per mm$^2$, about 10,000 per mm$^2$, about 5,000 per mm$^2$, or less. It is to be further understood that the density of the trans wells 16 in the support 26 can be between one of the lower values and one of the upper values selected from the ranges above.

The layout may also or alternatively be characterized in terms of the average pitch, i.e., the spacing from the center of a nanopore 20 to the center of an adjacent nanopore 20 (center-to-center spacing). The pattern can be regular such that the coefficient of variation around the average pitch is small, or the pattern can be non-regular in which case the coefficient of variation can be relatively large. In an example, the average pitch may range from about 100 nm to about 500 μm. The average pitch can be, for example, at least about 100 nm, about 5 μm, about 10 μm, about 100 μm, or more. Alternatively or additionally, the average pitch can be, for example, at most about 500 μm, about 100 μm, about 50 μm, about 10 μm, about 5 μm, or less. The average pitch for an example array including a particular pattern of nanopores 20 can be between one of the lower values and one of the upper values selected from the ranges above. In an example, the array has an average pitch (center-to-center spacing) of about 10 μm.

The trans wells 16 may be micro wells (having at least one dimension on the micron scale, e.g., about 1 μm up to, but not including, 1000 μm) or nanowells (having at least one dimension on the nanoscale, e.g., about 10 nm up to, but not including, 1000 nm). Each trans well 16 may be characterized by its aspect ratio (e.g., width or diameter divided by depth or height, respectively).

In an example, the aspect ratio of each trans well 16 may range from about 1:1 to about 1:5. In another example, the aspect ratio of each trans well 16 may range from about 1:10 to about 1:50. In an example, the aspect ratio of the trans well 16 is about 3.3.

The depth/height and width/diameter may be selected in order to obtain a desirable aspect ratio. The depth/height of each trans well 16 can be at least about 0.1 μm, about 1 μm, about 10 μm, about 100 μm, or more. Alternatively or additionally, the depth can be at most about 1,000 μm, about 100 μm, about 10 μm, about 1 μm, about 0.1 μm, or less. The width/diameter of each trans well 16 can be at least about 50 nm, about 0.1 μm, about 0.5 μm, about 1 μm, about 10 μm, about 100 μm, or more. Alternatively or additionally, the width/diameter can be at most about 1,000 μm, about 100 μm, about 10 μm, about 1 μm, about 0.5 μm, about 0.1 μm, about 50 nm, or less.

Each trans well 16 has an opening (e.g., that faces the cis well 12) that is large enough to accommodate at least a portion of the membrane 18 and the nanopore 20 that is associated therewith. For example, an end of the nanopore 20 may extend through the membrane 18 and into the opening of the trans well 16.

The cis well 12 and the trans wells 16 may be fabricated using a variety of techniques, including, for example, photolithography, nanoimprint lithography, stamping techniques, embossing techniques, molding techniques, microetching techniques, etc. As will be appreciated by those in the art, the technique used will depend on the composition and shape of the substrate 26 and the sidewall(s) 30. In an example, the cis well 12 may be defined by sidewall(s) 30 at an end 26 of the substrate 26, and the trans wells 16 may be defined through the substrate 26.

The membrane 18 may be any of the non-permeable or semi-permeable materials described herein. The membrane 18 is positioned between the cis well 12 and the trans wells 16, and thus provides a barrier between the wells 12, 16. The membrane may be positioned on the interstitial regions 42 of the substrate 26.

The nanopore(s) 20 may be any of the biological nanopores, solid state nanopores, and hybrid nanopores described herein. In one example, the nanopore(s) 20 is/are a modified nanopore 20' as described in reference to FIG. 3. As mentioned herein, each nanopore 20 fluidically connects a respective one of the trans wells 16 to the cis well 12. As such, the ratio of nanopores 20 to trans wells 16 is 1:1.

The nanopore 20 has two open ends and a hollow core or hole that connects the two open ends. The walls of the hollow core or hole are an inner surface 48 of the nanopore 20. When inserted into the membrane 18, one of the open ends of the nanopore 20 faces the cis well 12 and the other of the open ends of the nanopore 20 faces the trans well 16 and is aligned with at least a portion of the opening of trans well 16. The hollow core of the nanopore 20 enables the fluidic connection between the wells 12, 16. The diameter of the hollow core may range from about 1 nm up to 1 μm, and may vary along the length of the nanopore 20. In some examples, the open end that faces the cis well 12 may be larger than the open end that faces the trans well 16. In other examples, the open end that faces the cis well 12 may be smaller than the open end that faces the trans well 16.

The nanopore(s) 20 may be inserted into the membrane 18, or the membrane 18 may be formed around the nanopore(s) 20. In an example, the nanopore 18 may insert itself into a formed lipid bilayer (one example of the membrane 18). For example, a nanopore 20 in its monomeric form or polymeric form (e.g., an octamer) may insert itself into the lipid bilayer and assemble into a transmembrane pore. In another example, the nanopore 20 may be added to a grounded side of a lipid bilayer at a desirable concentration where it will insert itself into the lipid bilayer. In still another example, the lipid bilayer may be formed across an aperture in a polytetrafluoroethylene (PTFE) film and positioned between the cis and trans wells. The nanopore 20 may be added to the grounded cis compartment, and may insert itself into the lipid bilayer at the area where the PTFE aperture is formed. In yet a further example, the nanopore 20 may be tethered to a solid support (e.g., silicon, silicon oxide, quartz, indium tin oxide, gold, polymer, etc.). A tethering molecule, which may be part of the nanopore 20 itself or may be attached to the nanopore 20, may attach the nanopore 20 to the solid support. The attachment via the tethering molecule may be such that a single pore 20 is immobilized (e.g., between two chambers/wells). A lipid bilayer may then be formed around the nanopore 20.

The nanopore sensor device 10 includes an electrolyte solution 24 in the cis well 12 and the trans wells 16. Different examples of the device 10 disclosed herein include different examples of the electrolyte solution 24, which are described in more detail herein in reference to FIG. 2A through FIG. 4.

The nanopore sensor device 10 also includes electronics to individually and/or collectively address each of the trans electrodes 22. As mentioned herein, each of the trans well electrodes 22 is associated with a respective trans well 16 and a respective nanopore 20. Some of the electronics are schematically shown in the form of a circuit diagram in FIG. 1. The electronics include at least a stimulus source 52 and a controller 50. The stimulus source 52 is coupled to each of the plurality of trans electrodes 22 either individually, as depicted in FIG. 1, or via multiplexing, and the stimulus source 52 is to cause current to flow through one or more of the nanopores 20 by addressing the trans electrode 22 associated with a respective nanopore 20. The controller 50 is coupled to the stimulus source 52, and the controller 50 is configured to individually/selectively address one of the plurality of trans electrodes 22 (using the stimulus source) to cause an ionic current to flow through the nanopore 20 connected to the addressed trans electrode 22. In one example, each of the trans electrodes 22 is electrically connected to its own set of electronics, which include the stimulus source 52 and the controller 50. In another example, each of the trans electrodes 22 is electrically connected to a single stimulus source 52 and controller 50, which are connected to a multiplexer (not shown). As shown in FIG. 1, the electronics may also include amplifier(s) 54 to amplify electrical signals passing through respective nanopores 20 associated with trans electrodes 22 that are addressed.

Electrolyte Concentration

Referring now to FIG. 2A, one example of the nanopore sensor device 10 includes an electrolyte solution 24A in the cis well 12 and an electrolyte solution 24B in each of the trans wells 16, where the electrolyte solutions 24A, 24B have different concentrations of the reactive electrolyte species (represented by $C^+$, $A^-$) therein. For example, $C^+$ may represent a redox cation or a redox reductant ion and $A^-$ may represent a redox anion or a redox oxidant ion. More specifically, the concentration of the electrolyte $C^+$, $A^-$ in the electrolyte solution 24A within the cis well(s) 12 is higher than the concentration of the electrolyte $C^+$, $A^-$ in the electrolyte solution 24B within the trans well(s) 16. In these examples, the electrodes 14, 22 can be active electrodes or passive electrodes.

While the type of reactive electrolyte species $C^+$, $A^-$ in the electrolyte solutions 24A, 24B is the same, the concentration of the reactive electrolyte species $C^+$, $A^-$ in the electrolyte solutions 24A, 24B is different. More specifically, the concentration of the reactive electrolyte species $C^+$, $A^-$ in the electrolyte solution 24A that is to be introduced into or is contained in the cis well 12 is higher than the concentration of the reactive electrolyte species $C^+$, $A^-$ in the electrolyte solution 24B that is to be introduced into or is contained in the trans wells 16. In certain examples, a ratio of the electrolyte $C^+$, $A^-$ concentration in the electrolyte solution 24A (for the cis well 12) to the electrolyte $C^+$, $A^-$ concentration in the electrolyte solution 24B (for the trans wells 16) ranges from about 10:1 to about 3:1. In an example, the ratio of the electrolyte $C^+$, $A^-$ concentration in the electrolyte solution 24A (for the cis well 12) to the electrolyte $C^+$, $A^-$ concentration in the electrolyte solution 24B (for the trans wells 16) ranges from about 8:1 to about 5:1. In certain examples, the reactive electrolyte species $C^+$, $A^-$ concentration in the electrolyte solution 24A may range from about 300 mM to about 1000 mM, and the electrolyte $C^+$, $A^-$ concentration in the electrolyte solution 24B may be about 100 mM.

Each of the electrolyte solutions 24A, 24B also includes a polar solvent. In one example, the polar solvent is water. The different concentrations of the electrolyte $C^+$, $A^-$ are dissolved into the polar solvent to form the respective electrolyte solutions 24A, 24B.

In certain examples, the nanopore sensor device 10 may be stored with the electrolyte solution 24B having the same concentration of the electrolyte $C^+$, $A^-$ in the cis well 12 and in the trans wells 16. When it is desirable to utilize the nanopore sensor device 10, e.g., in a sensing operation, additional amounts of reactive electrolyte species may be introduced or swapped into the electrolyte solution 24A to form a higher concentration of the reactive electrolyte species $C^+$, $A^-$ in the cis well 12 (e.g., via a fluid inlet 56).

As such, one example disclosed herein is a nanopore sensor kit including an additional amount of reactive electrolyte species $C^+$, $A^-$ to be introduced into the one or more cis wells 12 through the fluid inlet 56 such that the one or more cis wells 12 contains the higher concentration of the electrolyte $C^+$, $A^-$ and the plurality of trans wells 16 contains the lower concentration of the electrolyte $C^+$, $A^-$ at an initial cycle of the nanopore sensor device 10.

When the respective electrolyte solutions 24A, 24B are contained within the cis well 12 and trans wells 16, a nucleotide sample may be added to the cis well 12, e.g., via the fluid inlet/outlet ports 56 and 58. The controller 50 may then be used to activate the stimulus source 52 to individually/selectively address one of the plurality of trans electrodes 22. The stimulus source 52 (e.g., a current source, a voltage source) causes an ionic current to flow through the nanopore(s) 20 that is/are connected to the addressed trans electrode 22. Due to the high reactive electrolyte species $C^+$, $A^-$ concentration in the cis well 12, the ionic current includes an amount of $A^-$ (e.g., redox anion, redox oxidant ions) of the reactive electrolyte species $C^+$, A-translocating through the nanopore 20 to the addressed trans well 16 that is higher than an amount of $C^+$ (e.g., redox cations, redox reductant ions) of the reactive electrolyte species $C^+$, $A^-$ translocating through the nanopore 20 from the addressed trans well 16.

In one example, the stimulus source 52 applies a voltage bias between the cis well(s) 12 and at least one of the plurality of trans wells 16 (using the electrodes 14, 22), and thus across the membrane 18. The voltage bias that is applied may be a positive polarity to the trans electrode 22 to attract negative charge compounds (such as negatively charge nucleotides, negatively charged labels/tags) in the cis well 12 towards the nanopore 20 and/or a negative polarity to the trans electrode 22 to repel negatively charged compounds (such as negatively charge nucleotides, negatively charged labels/tags) in the cis well 12 away from the nanopore 20. In an example, the voltage bias ranges from about −1 V to about 1 V between the cis well 12 an addressed one of the plurality of trans wells 16. Any voltage bias within the given range may be applied when the electrolyte solutions 24A, 24B are present in the respective wells 12, 16. In certain examples, the nanopore sensor device 10 operates in a bipolar mode (e.g., alternative current) providing a negative bias and a positive bias to the trans electrode 22. In certain examples, the nanopore sensor device 10 operates in a unipolar mode (e.g., direct current) providing a negative bias to the trans electrode 22.

The cis-trans voltage bias causes ionic current to flow through the nanopore(s) 20 associated with trans electrode(s) 22 that is/are addressed. In one example, the current flow across the nanopore(s) 20 forces the translocation of respective nucleotide(s) and/or tags/labels into the nanopore(s) 20 along with the reactive electrolyte species $A^-$ carrying the charge. As the nucleotide and/or label transits through the nanopore(s) 20, the current across the barrier changes due, for example, to blockage of the nanopore constriction 60 (see FIG. 3), change in resistance of the nanopore 20, and change in capacitance of the nanopores 20, for example. The signal from that change can be measured using an amplifier 54, or another known signal detection device. Depending upon the bias, the charge carrying reactive electrolyte species $A^-$ may be transported from the cis well 14 to the trans well 16.

In this example, the voltage polarity is typically applied such that the negatively charged nucleic acid and/or tag/label is electrophoretically driven into the nanopore(s) 20. In some instances, the voltage can be reduced, or the polarity reversed, to facilitate appropriate function.

When the reactive electrolyte species $C^+$, $A^-$ concentration is higher in the cis well 12 than in the trans wells 16, the reactive electrolyte species $C^+$ drift and diffusion currents are in opposite directions. A schematic of this is shown in FIG. 2B. With the higher reactive electrolyte species $C^+$ concentration on the cis side 12 at the initiation of sensing, the initial reactive electrolyte species $C^+$ current at t=0 is reduced and even eliminated. In this manner, the reactive electrolyte species $A^-$ are forced to carry the majority of the ionic current from t=0 onward, so the initial decrease in current is mitigated, and the overall current will remain more stable throughout the sensing run. The useful life of the nanopore sensor device 10 may be extended, in part because a greater proportion of the current is forced to be carrier through the nanopore 20 by the otherwise limiting reactive electrolyte species $A^-$. Additionally, the increased reactive electrolyte species $A^-$ concentration on the cis side 12 serves to increase the reactive electrolyte species $A^-$ diffusion current, thus maintaining a higher overall current.

Modified Nanopores

Figure 3:
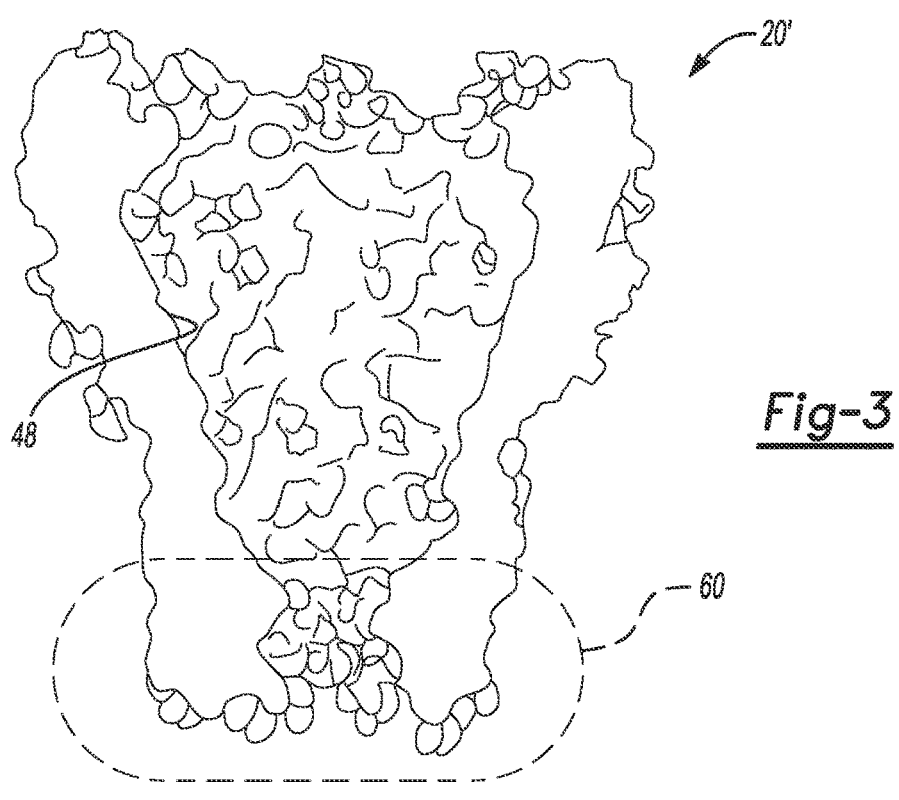
FIG. 3 is an enlarged and schematic view of a nanopore having a plurality of positively charged residues on an inner surface thereof.

Another example of the nanopore sensor device 10 includes a modified nanopore in the position of each of the nanopores 20. An example of the modified nanopore 20' is depicted in FIG. 3.

The modified nanopore 20' is protein or solid state nanopore whose inner surface 48 has been modified to introduce at least one fixed positive charge (referred to as positively charged residues) in place of a negative charge or a neutral charge. In protein nanopores, the positive charges may be introduced in the form of positively charged amino acid residues, such as arginine and lysine. Negatively charged amino acid residues and/or neutral amino acid residues can be mutated to the positively charged amino acid residues. The positive charges may also be introduced by mutating selected amino acid residues to cysteine, and then functionalizing the cysteine residues with a positive charge using a cysteine-reactive linker, such as maleimide. In solid state nanopores, the positive charges (or positively charged residues) may be introduced in the form of an organic positively charged species and/or an inorganic positively charged species (e.g., an $HfO_2$ coating). In other examples, the positively charged species may be grafted to the surface of the solid state nanopores via amino-silanes or other coupling agents.

The introduction of the positively charged residues to the inner surface 48 may exclude or reduce reactive electrolyte species $C^+$ from transporting through the modified nanopores 20'.

In one example, the modified nanopore 20' is a modified protein with negatively charged residues, neutral charged resides, or both negatively charged residues and neutral charged resides mutated to the positively charged residues. Many protein nanopores exhibit at least 7-fold symmetry, meaning that they are composed of seven or more identical polypeptide chains that assemble as a ring with symmetry determined by the number of individual chains. This symmetry can allow for the simultaneous mutation of each subunit of a single type of amino acid residue to completely alter the charge of the inner surface 48. In some instances, however, it may be desirable to mutate less than each subunit of the single type of amino acid residue, thus introducing fewer charges to the modified nanopore 20'. In these instances, it may be desirable to mutate some subunits (but not all 7, 8, etc.) of a particular residue, or by appropriately mutating a single-chain of the protein nanopore (e.g., point mutations).

As one example, the protein nanopore is MspA, which is octameric, i.e., has 8-fold symmetry. The positively charged residues may carry a charge or 1 or 2, which enables from 8 positive charges to 16 positive charges to be introduced at the inner surface 48 per residue type that is mutated (assuming all 8 of the residue are mutated). The MspA protein has an ultra-narrow (e.g., ~1 nm) and ultra-short (~2 nm) channel, and thus the addition of about 2.8 positive charges may be desirable for substantially reducing or eliminating reactive electrolyte species $C^+$ transport (see Example 4).

In one example, the negatively charged aspartic acid residues D139 and D118 of the MspA nanopore may be mutated to positively charged arginine or lysine. This positioning may aid in attracting a nucleotide sample to the modified nanopore 20' and also repel reactive electrolyte species $C^+$ that are present in the cis well 12.

In another example, the negatively charged aspartic acid residues D90, D91, and/or D93 of the MspA nanopore may be mutated to positively charged arginine or lysine. These residues reside at the narrow constriction zone 60 of the MspA nanopore. Thus, in some examples, the plurality of positively charged residues on the inner surface 48 is located at the constriction zone 60 of the modified nanopore 20'. As examples, the negatively charged aspartic acid residues D90, D91, and/or D93 may be respectively mutated to D90R, D91R, and/or D93R, which would introduce 1 or 2 positive charges per subunit. In other examples, the negatively charged aspartic acid residues D90, D91, and/or D93 may be respectively mutated to D90K, D91K, and/or D93K or D90H, D91H, and/or D93H. Any combinations of the D90, D91, and/or D93 mutations may also be made. Residues D90 and D91 are the most solvent-exposed, and thus may be the greatest determinant of cation repulsion when mutated to include the positively charged residues.

Table 1 sets forth additional examples of protein nanopores and proposed inner surface modifications that may enable reactive electrolyte species $C^+$ repulsion when used as the modified nanopores 20' in the nanopore sensor device 10. The proposed net charge equals the charge introduced if the proposed positively charged mutation were performed at each subunit of the negatively or neutrally charged residue being replace. As such, it may be desirable to mutate some subunits (but not all 7, 8, or 9) of a particular residue, or to mutate a single-chain or two chains of the protein nanopore (e.g., point mutations).

TABLE 1

| Protein NP | X-fold Symm. | Diameter/ Height (nm/nm) | Const. Zone Area (nm²) | Net Charge Density for C⁺ Repulsion | Proposed + Mutation | Proposed Net Charge |
|---|---|---|---|---|---|---|
| CsgG | 9 | 1.3/0.3 | 1.2 | 0.4 | F56R or F56K | +9 |
| #CsgGF | 9 | 1.5/1 | 4.7 | 1.4 | N17R | +9 |
| Fragacea-toxin C | 8 | 1.6/1 | 5.0 | 1.5 | D10R | +8 |

TABLE 1-continued

| Protein NP | X-fold Symm. | Diameter/ Height (nm/nm) | Const. Zone Area (nm²) | Net Charge Density for C⁺ Repulsion | Proposed + Mutation | Proposed Net Charge |
|---|---|---|---|---|---|---|
| Aerolysin | 7 | 1.3/9.3 | 38.0 | 11.4 | D216N and E254Q | +14 |
| *aerolysin | 7 | 1.3/1.3 | 5.3 | 1.6 | D216N and E222N or E254Q and E258Q | +14 |
| aHL | 7 | 1.2/5.5 | 20.7 | 6.2 | E111Q and D127N | +14 |
| *aHL | 7 | 1.2/1.3 | 4.9 | 1.5 | E111Q and D127N | +7 |

Denotes second constriction zone conferred by CsgF binding the CsgG pore
*Denotes circulation of only a small section of the overall constriction zone area The CsgG protein nanopore shares a narrow constriction zone 60 defined by residues N55 and F56, although this constriction happens within the middle of the larger pore where the surface is defined by the loop of residues 46-61. The measured dimensions of this pore are 1.3 nm diameter and 0.3 nm in height. A net charge of 0.4 may be sufficient to effect cation repulsion in this tiny channel (1.2 nm²). If CsgF peptides are added to the CsgG nanopore, a second constriction zone is formed approximately 3 nm below the first (going from cis to trans). This constriction zone is defined by residue N17. In this example, ion selectivity may be imparted at one or both constriction zones using the positive amino acid mutations disclosed herein.

The fragaceatoxin C nanopore is unique among ssDNA threading nanopores due to the alpha-helical nature of the transmembrane portion, which also defines the narrow constriction zone 60 where residue D10 imparts a negative charge. Cation repulsion may be achieved by mutating one or more of the eight D10 negatively charged residues.

Each of aerolysin and alpha-hemolysin (aHL) has a long and narrow barrel constriction zone 60 that, via symmetry, is defined by two-beta-strands. The internal surface charge of the barrel could be modulated to impart a net positive charge at any point throughout. Even with the 9.3 nm barrel height of the aerolysin pore, an overall net charge of >+11 could be achieved with two modest mutations, D216N and E254Q, which neutralize two negatively charged side chains on the barrel interior surface and effectively cap the barrel with two positive rings made by R282 and K242. The alpha-hemolysin barrel is smaller, about 5.5 nm in height, but could similarly be modulated to have positively charged rings on the entry and exit by neutralizing mutations, E111Q and D127N. In this example, the positive rings may be defined by residues K147 and K131.

In another example, the modified nanopore 20' is a solid-state nanopore with organic positively charged species, inorganic positively charged species, or both organic positively charged species and inorganic positively charged species as the positively charged residues. In one example, the inorganic positively charged species is an HfO₂ coating on the solid-state nanopores. In another example, amino-silanes (e.g., (3-aminopropyl)triethoxysilane, (3-aminopropyl)trimethoxysilane, (3-ethoxydimethylsilyl)propylamine, bis[3-trimethoxysilyl)propyl]amine, etc.) or lysine may be grafted to the surface to introduce the positive charge.

An example of a method of detecting an ionic current to analyze a biological compound includes providing a nanopores 20' within a membrane 18 separating a cis well 12 and a trans well 16, the nanopore 20' having a plurality of positively charged residues on an inner surface 48 of the nanopores 20'; providing an electrolyte 24 or 24A and 24B (respectively) within the cis well 12 and the trans well 16; and applying an electric current between a cis cathode 14 at least partially exposed to the cis well 12 and a trans anode 22 at least partially exposed to the trans well 16 to generate an ionic current through the nanopores 20', wherein the plurality of positively charged residues of the nanopore 20' inhibits translocation of reactive electrolyte species C⁺ from the trans well 16 to the cis well 12 during application of the electric current.

In some examples of this method, the electrolyte solution 24 may include any reactive electrolyte species C⁺, A⁻ that is capable of dissociating into counter ions (a cation C⁺ and its associated anion A⁻), wherein one of the counter ions, e.g., the cation C⁺ or the anion A⁻, participates in a half reaction at the cis electrode 14 and the trans electrode 22. This electrolyte solution 24 also includes a polar solvent, such as water.

In other examples of this method, the cis well 12 includes the electrolyte solution 24A (with the higher concentration of the reactive electrolyte species C⁺, A⁻) and the trans wells 16 include the electrolyte solution 24B (with the lower concentration of the reactive electrolytes species C⁺, A⁻). As such, the cis well 12 includes a higher concentration of the reactive electrolyte species C⁺, A⁻ than the trans well 16 during application of the electric current. When the modified nanopore 20' and the electrolyte solutions 24A, 24B are used together in the nanopore sensor device 10, several beneficial effects may be achieved: the magnitude of the fixed charge of the modified nanopore may be reduced (as opposed to when the same electrolyte solution 24 is used in the cis and trans wells 12, 16); the magnitude of the concentration gradient may be reduced (as opposed to when the non-modified nanopore 20 is utilized), which reduces the osmotic pressure differential across the membrane 18; and the nanopore current may increase.

When the electrolyte 24 or the respective electrolyte solutions 24A, 24B are contained within the cis well 12 and trans wells 16, a nucleotide sample may be added to the cis well 12, e.g., via the fluid inlet or outlets 56 and 58. The controller 50 may then be used to activate the stimulus source 52 to individually/selectively address one of the plurality of trans electrodes 22. The stimulus source 52 (e.g., a current source, a voltage source) causes an ionic current to flow through the modified nanopore(s) 20' that is/are connected to the addressed trans electrode 22.

In this example method, the application of the electric current between the cis cathode 14 and the trans anode 22 may be initiated by the stimulus source 52, which applies a voltage bias between the cis well(s) 12 and at least one of the plurality of trans wells 16 and across the membrane 18. In some examples, the applied electric current is a unipolar electric current. In other examples, the applied current is an alternating electric current between the cis electrode 14 and the addressed trans electrode 22 of the addressed trans well 16 of the plurality of trans wells 16. In this example, the voltage polarity is typically applied such that the negatively charged nucleic acid is electrophoretically driven into the modified nanopore(s) 20'. As an example, the voltage ranges from about 5 mV to about 500 mV (of either polarity).

The cis-trans voltage bias causes ionic current to flow through the modified nanopore(s) 20' associated with trans anode(s) 22 that is/are addressed. The current flow across the modified nanopore(s) 20' forces the translocation of respective nucleotide(s) through the modified nanopore(s) 20 along with the anions A-carrying the charge. The positively charged residues of the modified nanopore 20' may also help to attract the negatively charged nucleotides. Moreover, the positively charged residues may also be able to repel cations $C^+$ of the electrolyte solution 24 or 24A and 24B. Due to the cationic repulsion induced by the at least partially positively charged surface of the modified nanopore 20', the ionic current includes an amount of anions $A^-$ of the electrolyte $C^+$, $A^-$ translocating through the modified nanopore 20' to the addressed trans well 16 that is higher than an amount of cations $C^+$ of the electrolyte $C^+$, $A^-$ translocating through the modified nanopore 20' from the addressed trans well 16. This effect may be enhanced when the varying concentration electrolyte solutions 24A, 24B are used in combination with the modified nanopore 20'.

The modified nanopores 20' reduces or retards transport of the cations $C^+$ through the nanopore 20', either via drift or diffusion. As such, the initial cation C+ current at t=0 is reduced and even eliminated. In this manner, the anions $A^-$ are forced to carry the majority of the ionic current from t=0 onward, so the initial decrease in current is mitigated, and the overall current will remain more stable throughout the sensing run. The useful life of the nanopore sensor device 10 may be extended, in part because a greater proportion of the current is forced to be carrier through the nanopore 20 by the otherwise limiting anions $A^-$.

Redox-Inactive Buffer

Figure 4:
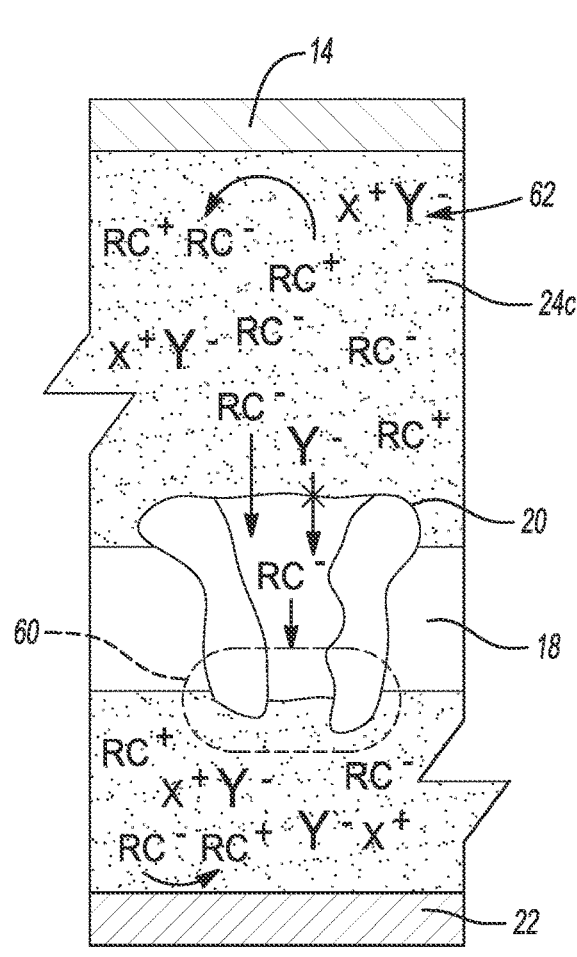
FIG. 4 is an enlarged and schematic view of a portion of the nanopore sensor device, where the electrolyte solution includes a redox couple and a redox-inactive buffer ions having a diameter greater than a diameter of a constriction zone of the nanopore.

Referring now to FIG. 4, one example of the nanopore sensor device 10 includes an electrolyte solution 24C (in the cis well 12 and each of the trans wells 16) that includes a redox-inactive buffer 62, which includes a redox inactive species (e.g., cation $X^+$, anion $Y^-$) having a diameter that is greater than a diameter of the constriction zone 60 of the nanopore 20 or 20'; and a redox couple (e.g., $RC^+$, $RC^-$). In these examples, the electrodes 14, 22 are selected to be an inactive material that can transfer electrons rather than exchange ions.

In these examples, the electrolyte solution 24C includes a redox couple $RC^+$, $RC^-$. With a redox couple, the same reactant RC can undergo reduction and oxidation, and both the oxidized form ($RC^+$) and the reduced form ($RC^-$) can exist in the electrolyte solution. Any redox couple $RC^+$, $RC^-$ may be used that can transfer electrons. Examples of suitable redox couples include FeCN (e.g., $[Fe(CN)_6]^{3-} + e^- \rightleftharpoons [Fe(CN)_6]^{4-}$). Since the FeCN redox couples are both negatively charged, counterions are included to maintain the overall electrical neutrality of the solution 24C. Examples of suitable counter ions that may be present include $Na^+$, $Li^+$, $Ca^{2+}$, $K^+$. The electrolyte solution 24C also includes a polar solvent, such as water.

When the redox couple is positively charged, the cation $X^+$ of the redox-inactive buffer 62 is selected such that it has a diameter greater than the diameter of the nanopore constriction zone 60. This bulky redox-inactive cation $X^+$ will be too large to transport through the nanopore 20, and thus will not deleteriously affect the balance of the positively charged redox couple.

The bulky redox-inactive cation $X^+$ includes a cation complexing agent and a cation complexed at the center of the cation complexing agent. The diameter of a center cavity of the cation complexing agent is selected to match the size of the cation. By "match," it is meant the cation can fit within the center cavity, and that the atoms of the cation complexing agent can complex with the cation.

Examples of suitable cation complexing agents include crown ethers, calixarenes, and valinomycin. Examples of suitable crown ethers include:

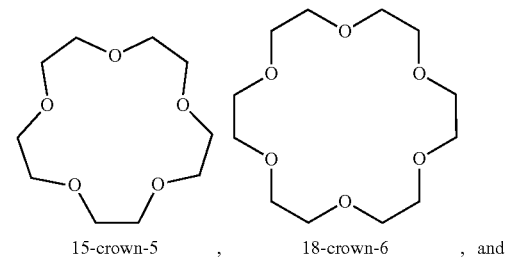

15-crown-5     ,     18-crown-6     , and

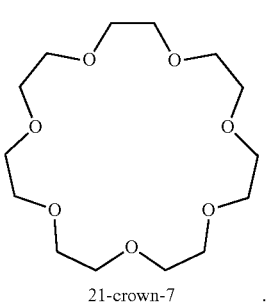

21-crown-7     .

It is to be understood that derivatives of these crown ethers may also be used, such as benzo- or dibenzo-15-crown-5, benzo- or dibenzo-18-crown-6, benzo- or dibenzo-21-crown-7, dicyclohexano-18-crown-6, dicyclohexano-21-crown-7, or the like. Azacrowns (e.g., aza-15-crown-5) or thiacrowns may also be used. Examples of suitable calixarenes include and $C_3Cal-5$, $C_3Cal-6$, and calix[4]arene tetraesters. Valinomycin is shown below:

Examples of matching cations and cation complexing agents are shown in Table 2.

TABLE 2

| Cation | Cation Diameter | Crown Ethers (center cavity diameter) | Calix-arenes | Valino-mycin |
|--------|-----------------|----------------------------------------|--------------|--------------|
| K$^+$ | ~266 pm | 18-crown-6 (from about 260 pm to about 320 pm) | C$_3$Cal-5 C$_3$Cal-6 | Can complex both, but has greater selectively for K$^+$ over Na$^+$ |
| Na$^+$ | from about 194 pm to about 204 pm | 15-crown-5 (from about 170 pm to about 220 pm) | Calix[4]-arene tetraesters | |

The amount of the cation complexing agent may vary depending, at least in part, upon the affinity of the complexing agent for the cation in the redox inactive buffer 62. Taking into account this affinity, the cation complexing agent may be used in any suitable amount that will result in the complexation of at least 99% of the available cation to create the bulky redox-inactive cation X$^+$. Generally, the molar concentration of the cation complexing agent may range from greater than 0 mM to about 1M. In an example, 18-crown-6 may be used in a potassium-containing electrolyte in a molar concentration ranging from about 50 mM to about 500 mM. In a more specific example, 18-crown-6 may be used in a potassium-containing electrolyte in a molar concentration of about 300 mM. In another example, calixarenes may be used in a potassium-containing or sodium-containing electrolyte in a molar concentration ranging from greater than 0 mM to about 20 mM. Any of the concentrations used may depend upon the solubility of the cation complexing agent in the electrolyte solution 24C.

When the redox couple is positively charged, the anion Y$^-$ of the redox-inactive buffer 62 may be any anion that is redox inactive at the electrodes 14, 22 of the nanopore sensor device 10. Any anion Y$^-$ may be used as the electrodes 14, 22 are inactive. In an example, the anion Y$^-$ is a chloride ion.

When the redox couple is negatively charged, the anion Y$^-$ of the redox-inactive buffer 62 is selected such that it has a diameter greater than the diameter of the nanopore constriction zone 60. This bulky redox-inactive anion Y$^-$ will be too large to transport through the nanopore 20 or the modified nanopore 20', and thus will not deleteriously affect the balance of the negatively charged redox species.

When the redox species is negatively charged, the cation X$^+$ of the redox-inactive buffer 62 may be any cation that is redox inactive at the electrodes 14, 22 of the nanopore sensor device 10. Any cation C$^+$ may be used as the electrodes 14, 22 are inactive. Examples of suitable cations that may be present include Na$^+$, Li$^+$, Ca$^{2+}$, K$^+$.

When the electrolyte 24C is contained within the cis well 12 and trans wells 16, a nucleotide sample may be added to the cis well 12, e.g., via the fluid inlet or outlet 56 and 58. The controller 50 may then be used to activate the stimulus source 52 to individually/selectively address one of the plurality of trans anodes 22. The stimulus source 52 (e.g., a current source, a voltage source) causes an ionic current to flow through the nanopore(s) 20 or modified nanopore(s) 20' that is/are connected to the addressed trans anode 22.

In one example, the stimulus source 52 applies a voltage bias between the cis well(s) 12 and at least one of the plurality of trans wells 16 (using the electrodes 14, 22), and thus across the membrane 18. The magnitude and polarity (positive or negative) of the voltage bias that is applied may depend, in part, upon the concentration of the redox couple in the electrolyte solution 24C. The magnitude and polarity may be adjusted in order to account for the diffusivity and mobility of the redox couple. In an example, the voltage bias ranges from about −1 V to about 1 V between the cis well 12 an addressed electrode 22 of one of the plurality of trans wells 16. Any voltage bias within the given range may be applied when the electrolyte solution 24C is present in the respective wells 12, 16.

In some examples, the controller 50 is configured to cause the stimulus source 52 to apply a unipolar electric current between the cis electrode 14 and the addressed trans electrode 22 of the addressed trans well 16 of the plurality of trans wells 16. As one example, when the redox couple is negatively charged and thus is the desired species for carrying the charge, a positive electric current is induced between the wells 12, 16 and thus across the nanopore 20 or 20' and membrane 18. As another example, when the redox couple is positively charged and thus is the desired species for carrying the charge, a negative electric current is induced between the wells 12, 16 and thus across the nanopore 20 or 20' and membrane 18. In other examples, the controller 50 is configured to cause the stimulus source 52 to apply an alternating electric current between the cis electrode 14 and the addressed trans electrode 22 of the addressed trans well 16 of the plurality of trans wells 16.

The cis-trans voltage bias causes ionic current to flow through the nanopore(s) 20 or 20' associated with trans electrode(s) 22 that is/are addressed. The current flow across the nanopore(s) 20 or 20' forces the translocation of respective nucleotide(s) through the modified nanopore(s) 20 or 20' along with the negatively charged redox couple carrying the charge. The bulky ions of the inactive redox buffer 62 are too large to translocate the nanopore 20 or 20'.

When the modified nanopore 20' is used in this example, the positively charged residues of the modified nanopore 20' may help to attract the negatively charged nucleotides, as well as repel cations C$^+$ of the redox-inactive buffer 62 as well as cations used in conjunction with the redox couple. Due to the cationic repulsion induced by the at least partially positively charged surface of the modified nanopore 20', the ionic current includes an amount of anions RC$^-$ of the redox couple translocating through the modified nanopore 20' to the addressed trans well 16 that is higher than an amount of anions $A^-$ of the redox-inactive buffer 62 translocating through the modified nanopore 20' from the addressed trans well 16.

To further illustrate the present disclosure, an example is given herein. It is to be understood that this example is provided for illustrative purposes and is not to be construed as limiting the scope of the present disclosure.

NON-LIMITING WORKING EXAMPLES

Comparative Example 1

In this comparative example, the behavior of a nanopore sensor with the same $K^+Cl^-$ concentration in the cis and trans wells was computed. The time and species dependence of the nanopore current was obtained by numerically solving the Nernst-Planck equation in a commercial software package (Comsol).

The calculation was performed for a nanopore sensor with a cis well having a diameter of 200 μm and a height of 200 μm, a trans well having a diameter of 20 μm and a height of 20 μm, a $K^+Cl^-$ concentration of 100 mM in each of the well, and a cis-trans voltage bias of about 200 mV.

Figure 5A:
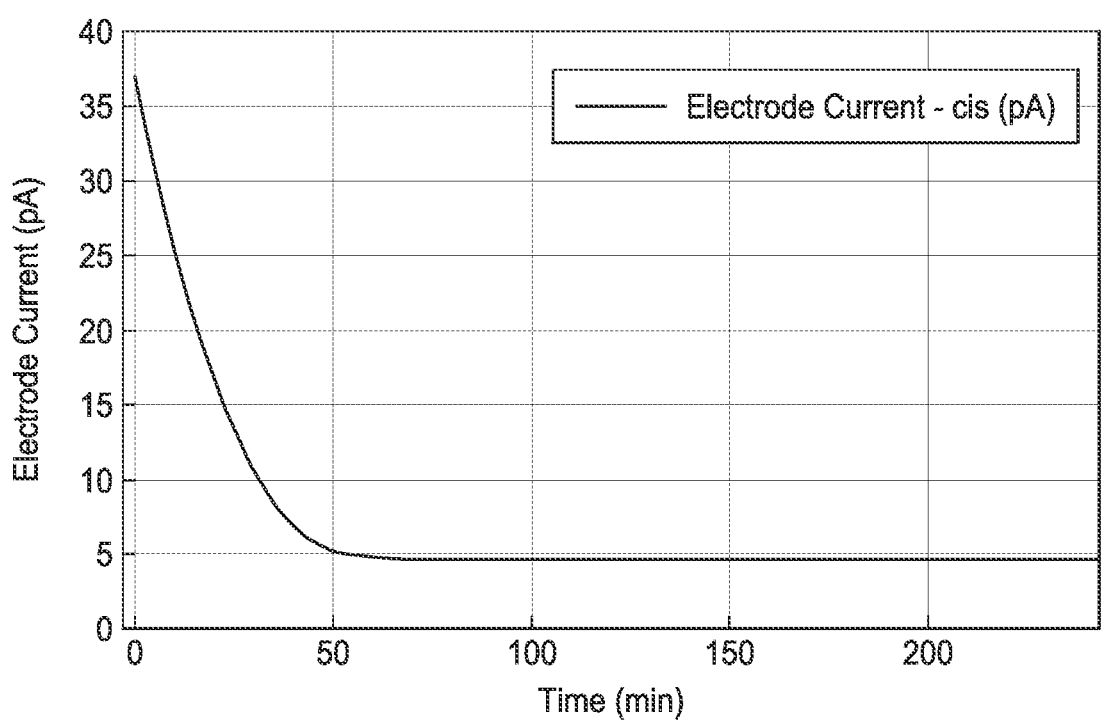
FIG. 5A and FIG. 5B are graphs depicting the simulated time dependence of the current (5A; electrode current (pA) versus time (min)) and the simulated species breakdown of the current components (5B; current (pA) versus time (min)) for a comparative nanopore sensor device including the same $K^+Cl^-$ concentration in the cis and trans wells.
Figure 5B:
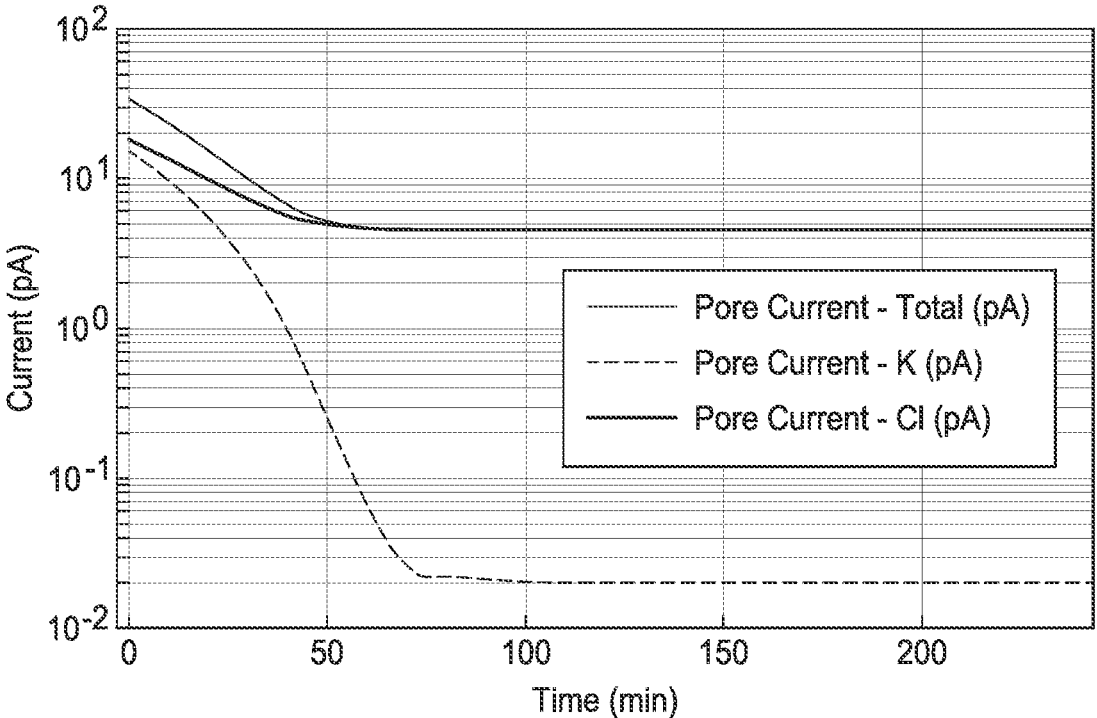

FIG. 5A depicts the time dependence of the current and FIG. 5B depicts the species breakdown of the current components.

From this simulation, it was evident that the current rapidly decayed over a period of about 50 minutes, which was consistent with the calculation from Eq. (1) (which was performed using the parameters set forth in this example and using chloride as the reactive species). As shown in FIG. 5B, at time t=0, the current was carried equally by the $K^+$ cation and the $Cl^-$ anion. Over time, both components declined, with the cationic component declining much more rapidly to the point where the current was carried almost exclusively by the anion. At that point, the supply and consumption of the $Cl^-$ anion was balanced and a new equilibrium was reached. However, this new equilibrium was at a much lower current level (e.g., about 15% of the initial current) that would not be practically usable for the nanopore sensor device.

Example 2

In this example, the behavior of a nanopore sensor with a higher $K^+Cl^-$ concentration in the cis well than in the trans well was computed. The time and species dependence of the nanopore current was obtained by numerically solving the Nernst-Planck equation in a commercial software package (Comsol).

The calculation was performed for a nanopore sensor with a cis well having a diameter of 200 μm and a height of 200 μm, a $K^+Cl^-$ concentration of 500 mM in the cis well, a trans well having a diameter of 20 μm and a height of 20 μm, a $K^+Cl^-$ concentration of 100 mM in the trans well, and a cis-trans voltage bias of about 80 mV.

Figure 6A:
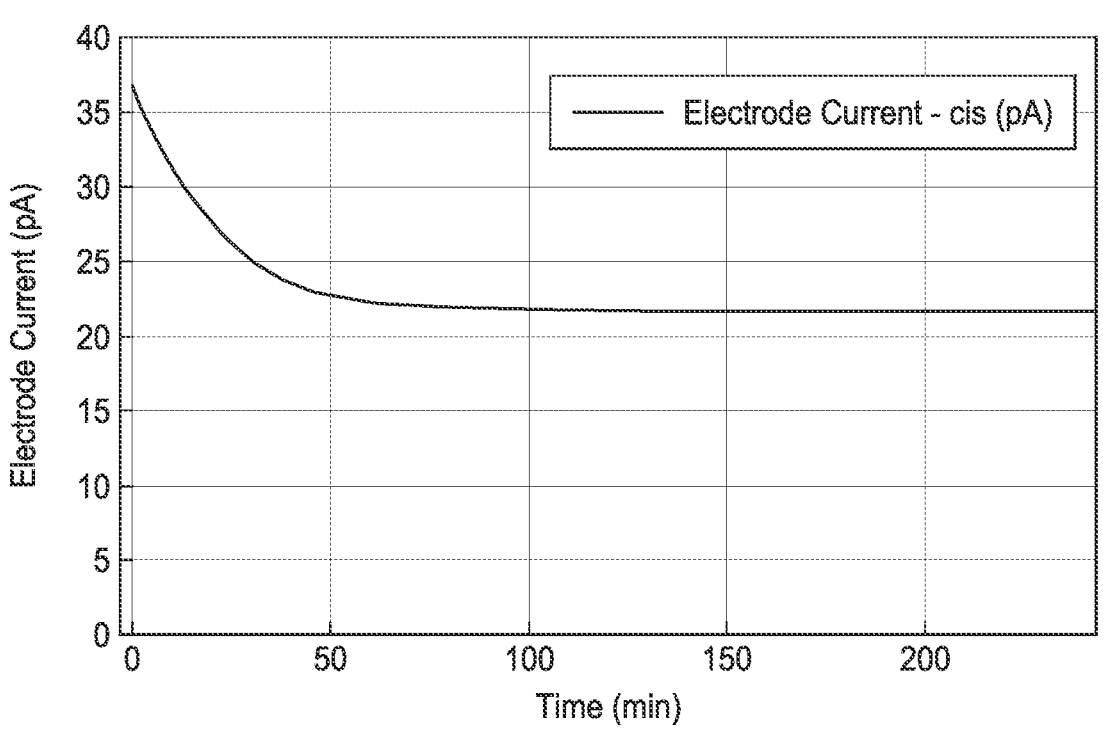
FIG. 6A and FIG. 6B are graphs depicting the simulated time dependence of the current (6A; electrode current (pA) versus time (min)) and the simulated species breakdown of the current components (6B; current (pA) versus time (min)) for an example nanopore sensor device including a higher $K^+Cl^-$ concentration in the cis well than in the trans well.
Figure 6B:
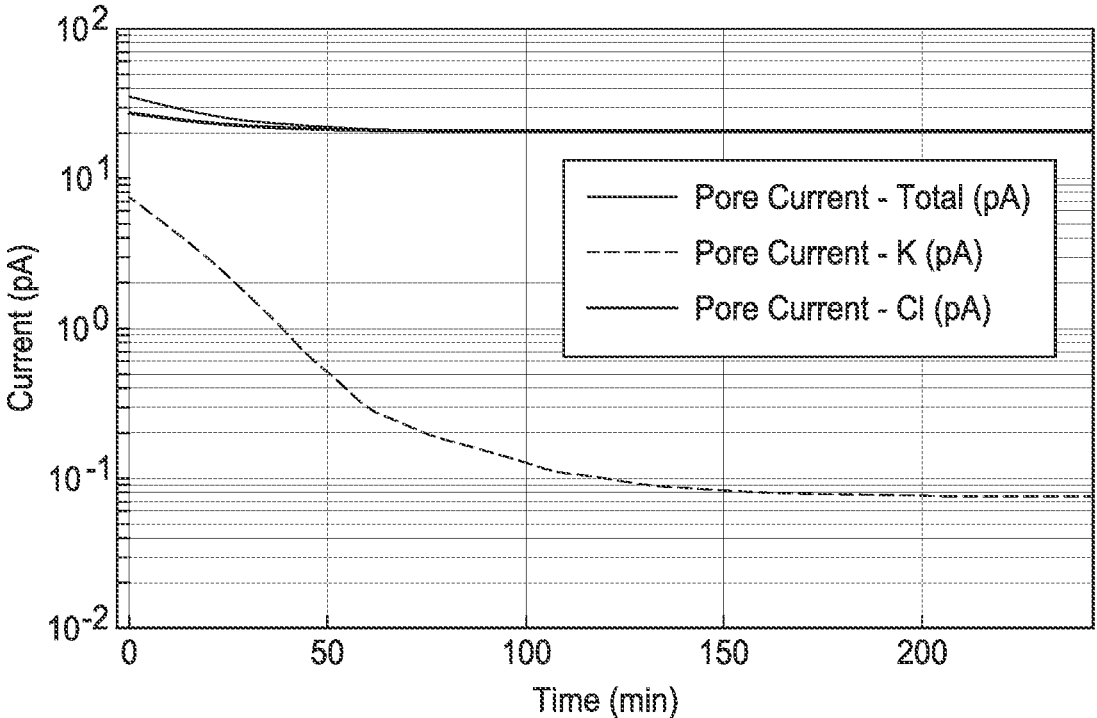

FIG. 6A depicts the time dependence of the current and FIG. 6B depicts the species breakdown of the current components.

As shown in FIG. 6B, at time t=0, the portion of the current due to the chloride anion was 10× larger than that of the potassium cation, resulting in an equilibrium condition (~60% of the initial current) that would be practically useful, unlike the comparative example (with an equal electrolyte concentration in the cis and trans wells).

Example 3

In this example, the behavior of another nanopore sensor with a higher $K^+Cl^-$ concentration in the cis well than in the trans well was computed. The time and species dependence of the nanopore current was obtained by numerically solving the Nernst-Planck equation in a commercial software package (Comsol).

The calculation was performed for a nanopore sensor with a cis well having a diameter of 200 μm and a height of 200 μm, a $K^+Cl^-$ concentration of 850 mM in the cis well, a trans well having a diameter of 20 μm and a height of 20 μm, a $K^+Cl^-$ concentration of 100 mM in the trans well, and a cis-trans voltage bias of about 55.35 mV.

Figure 7A:
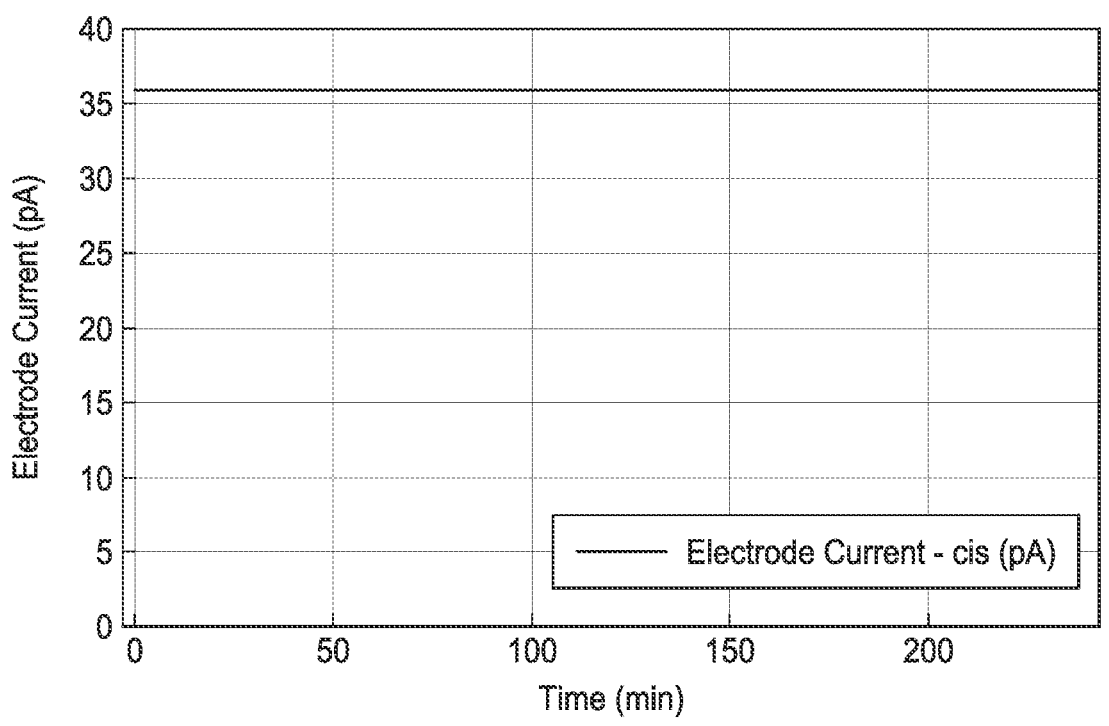
FIG. 7A and FIG. 7B are graphs depicting the simulated time dependence of the current (7A; electrode current (pA) versus time (min)) and the simulated species breakdown of the current components (7B; current (pA) versus time (min)) for another example nanopore sensor device including a higher $K^+Cl^-$ concentration in the cis well than in the trans well.
Figure 7B:
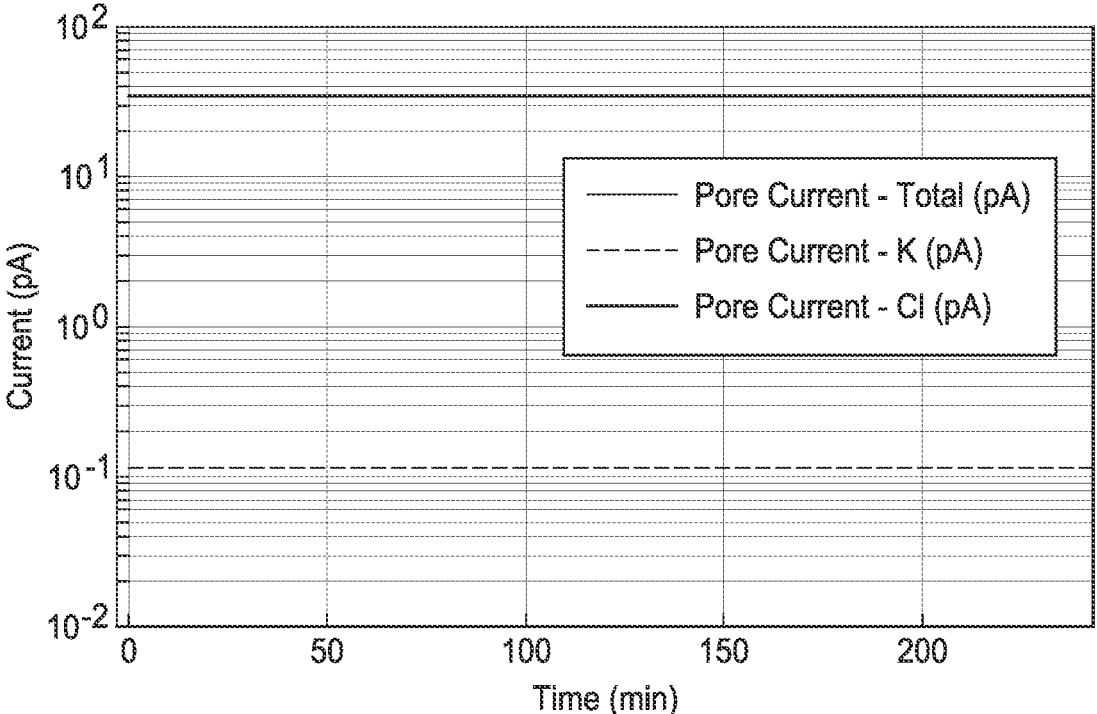

FIG. 7A depicts the time dependence of the current and FIG. 7B depicts the species breakdown of the current components.

As shown in FIG. 7B, the $K^+$ transport throughout the pore was nearly three orders of magnitude lower than the $Cl^-$ component, and thus the supply and consumption of $Cl^-$ was balanced, and the pore current was stable. In this example, the concentration gradient and cis-trans bias completely balanced out the drift and diffusion cation currents, yet the total current was approximately equal to that of the Comparative example 1.

Example 4

To assess whether the ultra-narrow but ultra-short channels of biological nanopores can exclude cations at desired levels, 3D finite element analysis was performed on the geometry, as shown in FIG. 8. The full structure is rotationally symmetric, and thus only half the simulation domain in shown in FIG. 8.

In this analysis, the nanopore was 1 nm wide and 2 nm tall, which approximates the dimensions of the MspA constriction. A fixed surface charge in varying amounts was placed on the surface of the constriction. The "cis" and "trans" wells were placed under boundary conditions that simulated an infinite source of $K^+$ and $Cl^-$ in order to eliminate depletion effects from the simulations.

The simulations were performed for surface charge densities in the range of 0.01 $q/nm^2$ to 1 $q/nm^2$, where q is the elementary charge. This is the net charge that would be present in an idealized "dry" state in the absence of electrolytes. Such charge densities should, in principle, be achievable in protein nanopores.

Figure 10:
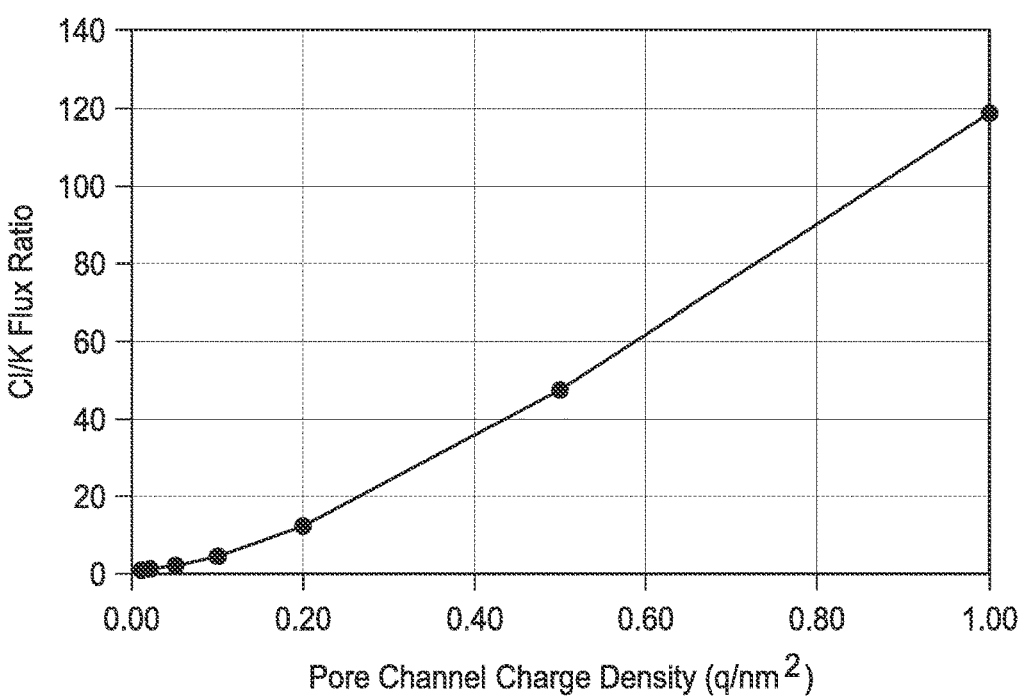
FIG. 10 is a graph depicting the computed dependence of the Cl:K flux ratio through the nanopore on the magnitude of the fixed charge density in the pore channel.

The results of the simulation are shown in FIG. 9A, FIG. 9B, and FIG. 9C, respectively, for σ=0.01 $q/nm^2$, σ=0.1 $q/nm^2$, and σ=1 $q/nm^2$. More specifically, FIG. 9 illustrates the computed spatial distribution (log scale) of the Cl:K ratio in the simulation domain. The data in in FIG. 9A, FIG. 9B, and FIG. 9C is plotted on a log scale and a scale marker accompanies each image. While the Cl:K ratio peaks in the nanochannel for all three conditions, the magnitude of the effect is exponentially dependent on the charge density. This is more clearly visible in FIG. 10. FIG. 10 is the computed dependence of the Cl:K flux ratio through the nanopore on the magnitude of the fixed charge density in the pore channel.

Figure 11A:
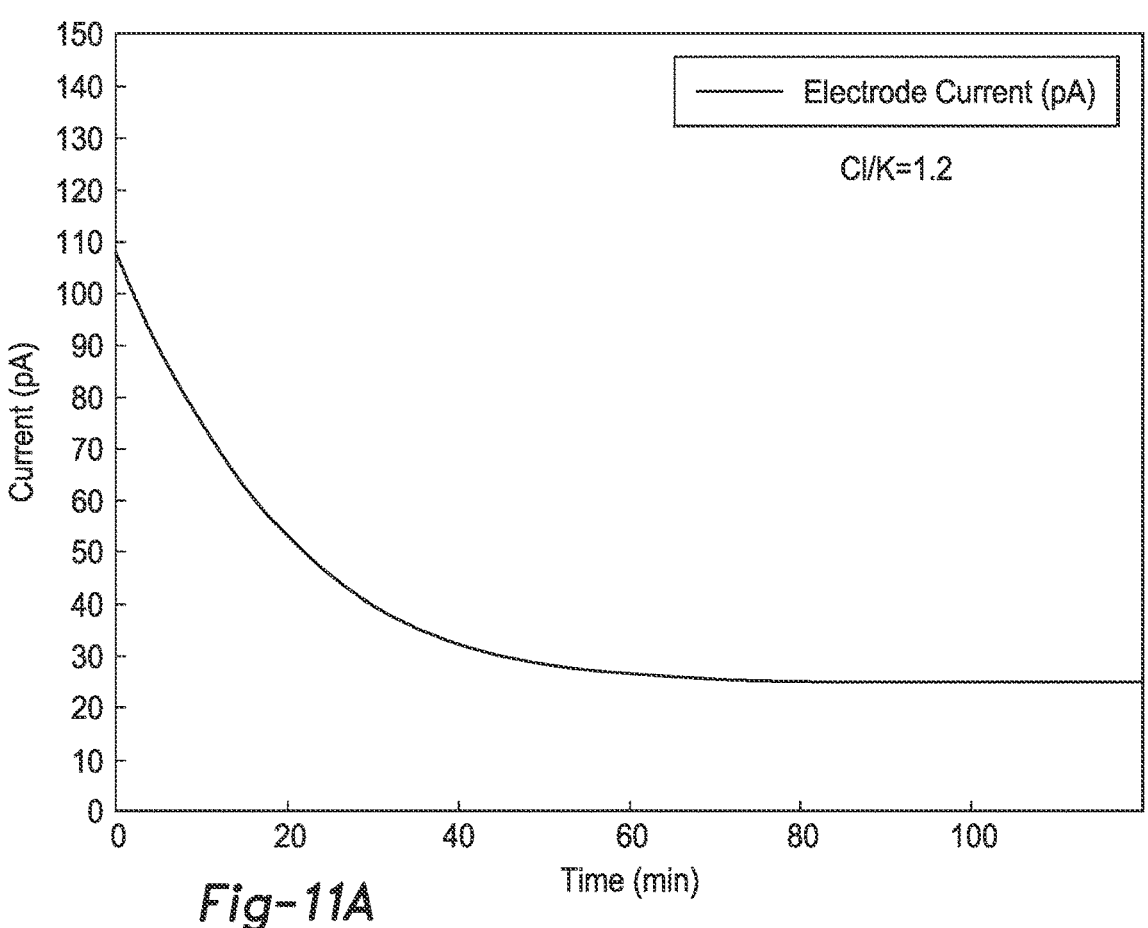
FIGS. 11A through 11C are graphs depicting the computed dependence of a nanopore sensor with a modified nanopore at various Cl:K flux ratios.
Figures 11B, 11C:
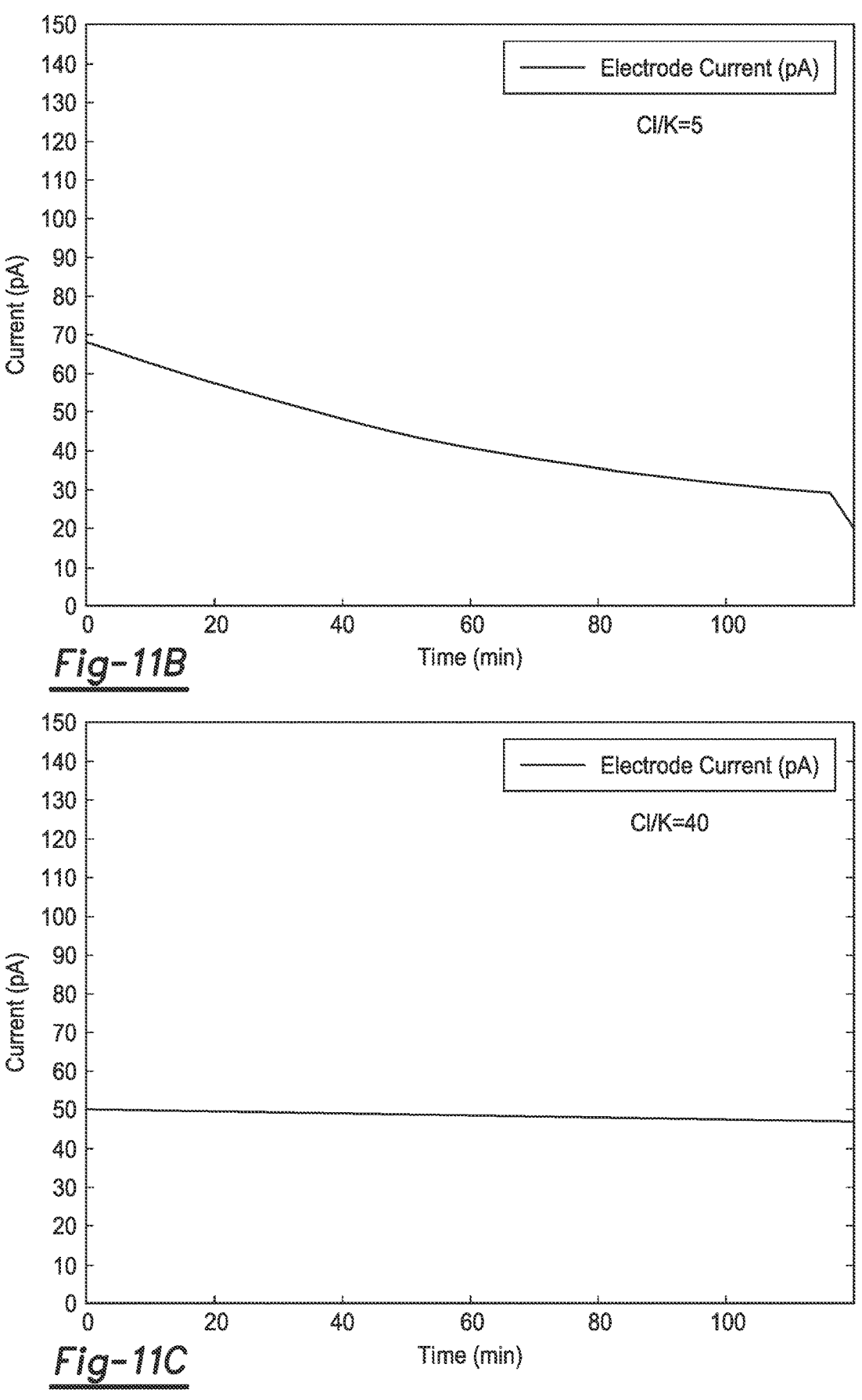

In order to characterize the beneficial effect of suppressing the total $K^+$ flux through the nanopore, additional simulations were performed as described in Example 1 (a cis well of D=200 μm/H=200 μm; trans well of D=20 μm/H=20 μm; 100 mM $K^+Cl^-$ in the cis and trans wells; and a cis-trans bias of 100 mV) at three different values of the Cl:K flux ratio: R=1.2 (σ=0.01 q/nm2); R=5 (σ=0.1 $q/nm^2$); and R=40 (σ=0.4 $q/nm^2$). The results are show in in FIG. 11A, FIG. 11B, and FIG. 11C, respectively. From these results, the beneficial effect of suppressing $K^+$ transport through the nanopore is clear. At R=40 (σ=0.4 $q/nm^2$) the depletion effects were nearly completely suppressed. The current drift was significantly reduced, which facilitates practical use of the nanopore sensor.

Example 5

In this example, four different types of modified MspA pores were compared. The comparative MspA pores included neutral asparagine residues at D90, D91, and D93. The first example MspA pores included neutral asparagine residues at D90 and D93 and a positively charged arginine residue at D91. The second example MspA pores included neutral asparagine residues at D91 and D93 and a positively charged arginine residue at D90. The third example MspA pores included a neutral asparagine residue at D93 and positively charged arginine residues at D90 and D91. All of the pores were tested using wells that were 5 μm deep and 16 μm wide. The data presented in this example represents the average results for ten or more of the respective pores (e.g., 19 comparative MspA pores were tested at 150 mM, 58 first example MspA pores were tested at 150 mM, 21 comparative MspA pores were tested at 300 mM, and 10 first example MspA pores were tested at 300 mM).

Figure 12B:
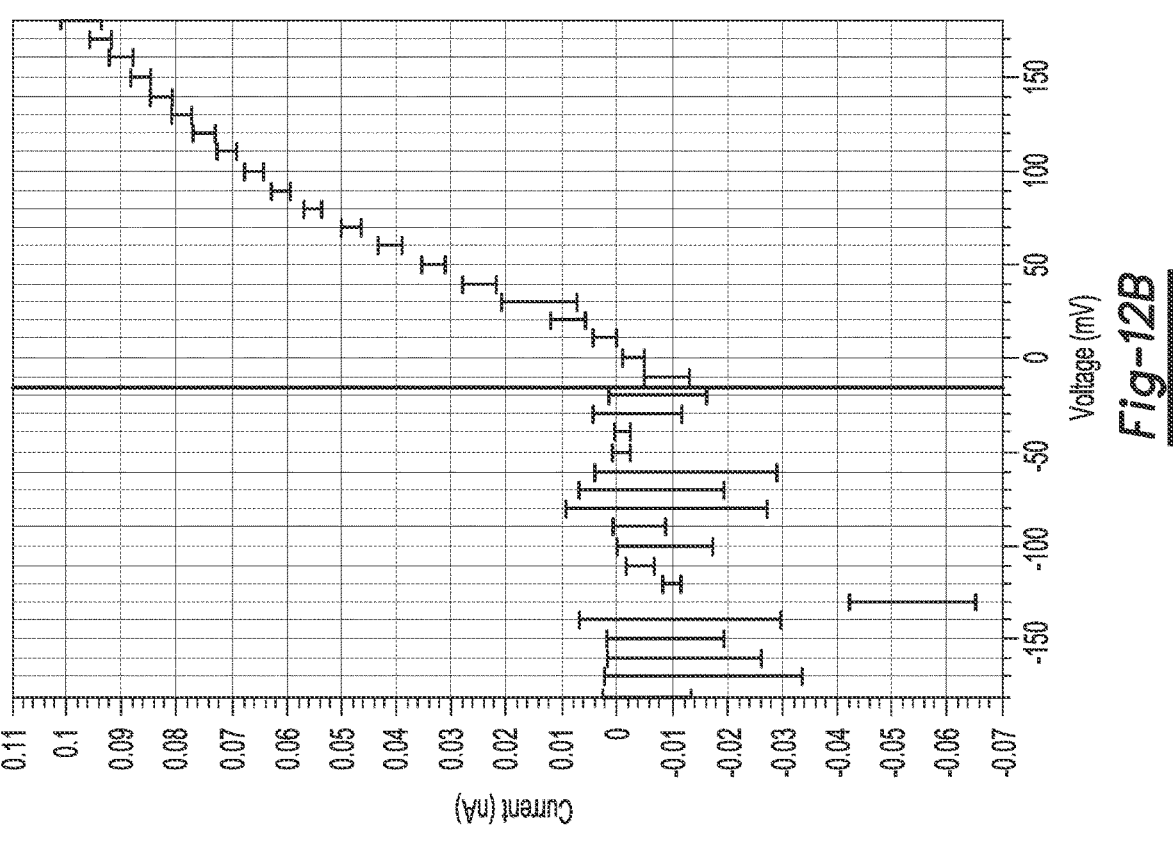
FIG. 12B is a graph depicting the current (nA, Y axis) versus voltage (mV, X axis) for first example MspA pores.
Figure 12A:
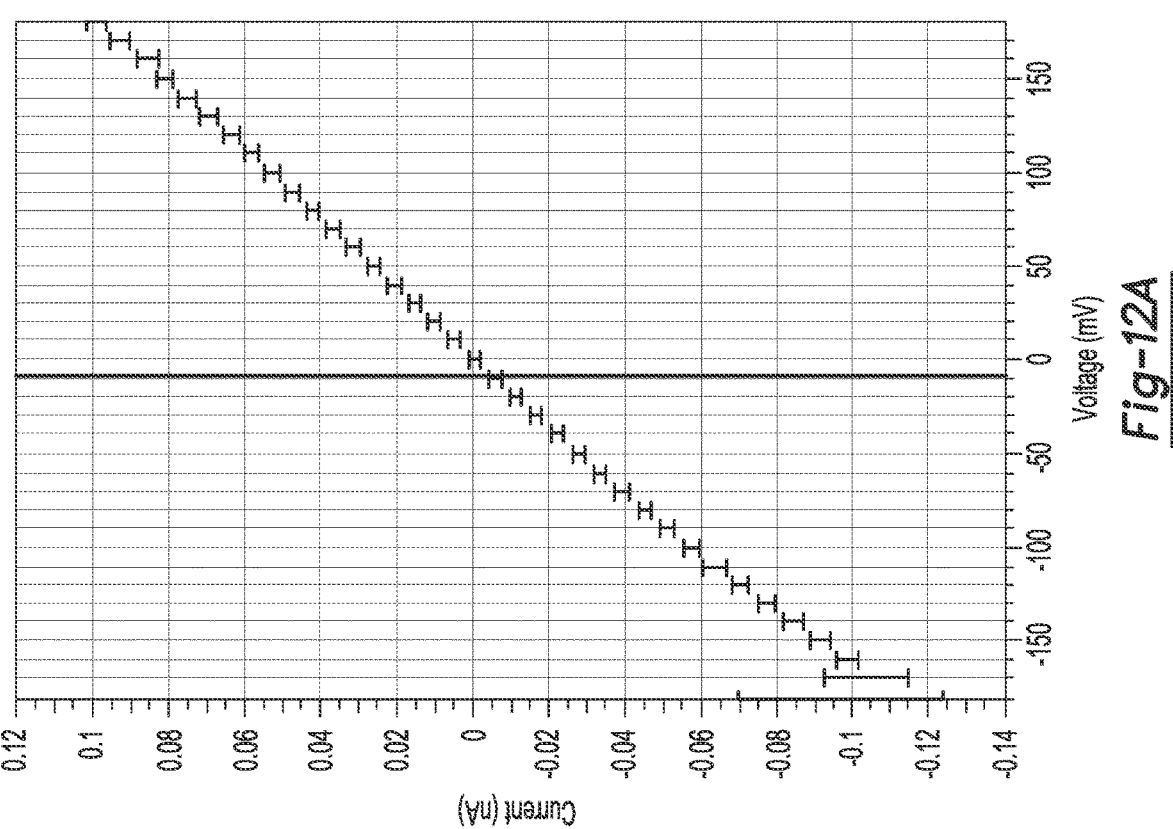
FIG. 12A is a graph depicting the current (nA, Y axis) versus voltage (mV, X axis) for comparative MspA pores.

In the first experiment, the $K^+Cl^-$ concentration in the cis and trans wells was 300 mM. The cis-trans voltage bias was swept from −175 mV to 175 mV and the current (nA) was recorded. FIG. 12A depicts the current (nA, Y axis) versus voltage (mV, X axis) for the comparative MspA pores and FIG. 12B depicts the current versus voltage graph for the first example MspA pores. While the data for the second and third example MspA pores is not reproduced herein, all of the pores (comparative and example MspA pores), exhibited higher resistance at higher positive potentials. The first and second example MspA pores (each having two neutral residues) exhibited an expected rectification of current at the negative bias (see FIG. 12B for the results of the first example MspA pores). The third example MspA pores (having two positive residues) exhibited almost no conductivity until large positive potentials were used.

Figure 13:
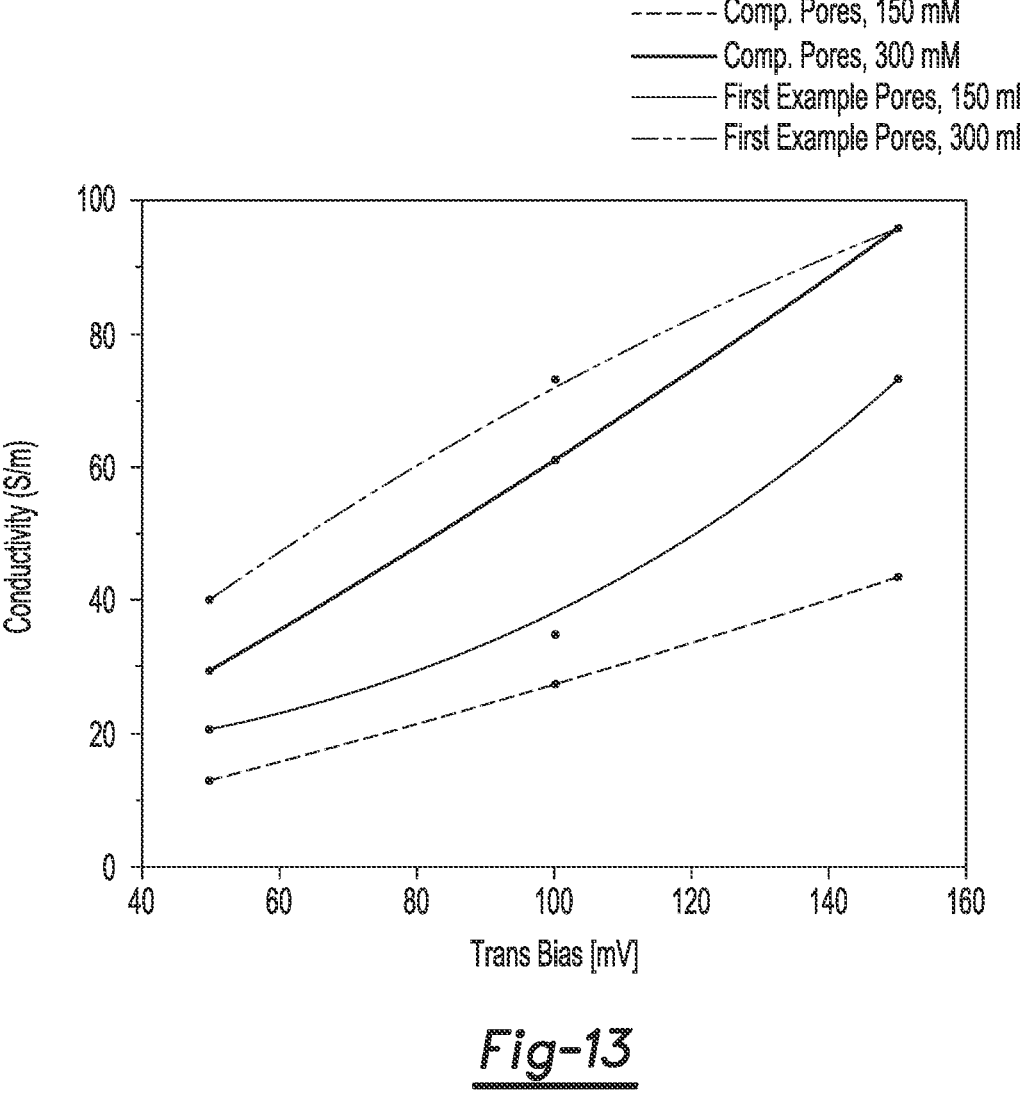
FIG. 13 is a graph depicting the average conductivity (S/m, Y axis) of the first example pores and of the comparative pores versus the cis-trans voltage bias (mV, X axis) using different concentrations of a KCl electrolyte.

In the second experiment, the comparative MspA pores and the first example MspA pores were tested with different $K^+Cl^-$ concentrations, namely 150 mM and 300 mM. The bias voltage was swept from 50 mV to 150 mV and the current (pA) was recorded. FIG. 13 plots the average current (pA, Y axis) of the first example pores and of the comparative pores versus the cis-trans voltage bias (mV, X axis) in the different electrolytes. Clearly, the first example MspA pores had higher conductivity than the comparative MspA pores, regardless of the electrolyte concentration.

Figures 14A, 14B:
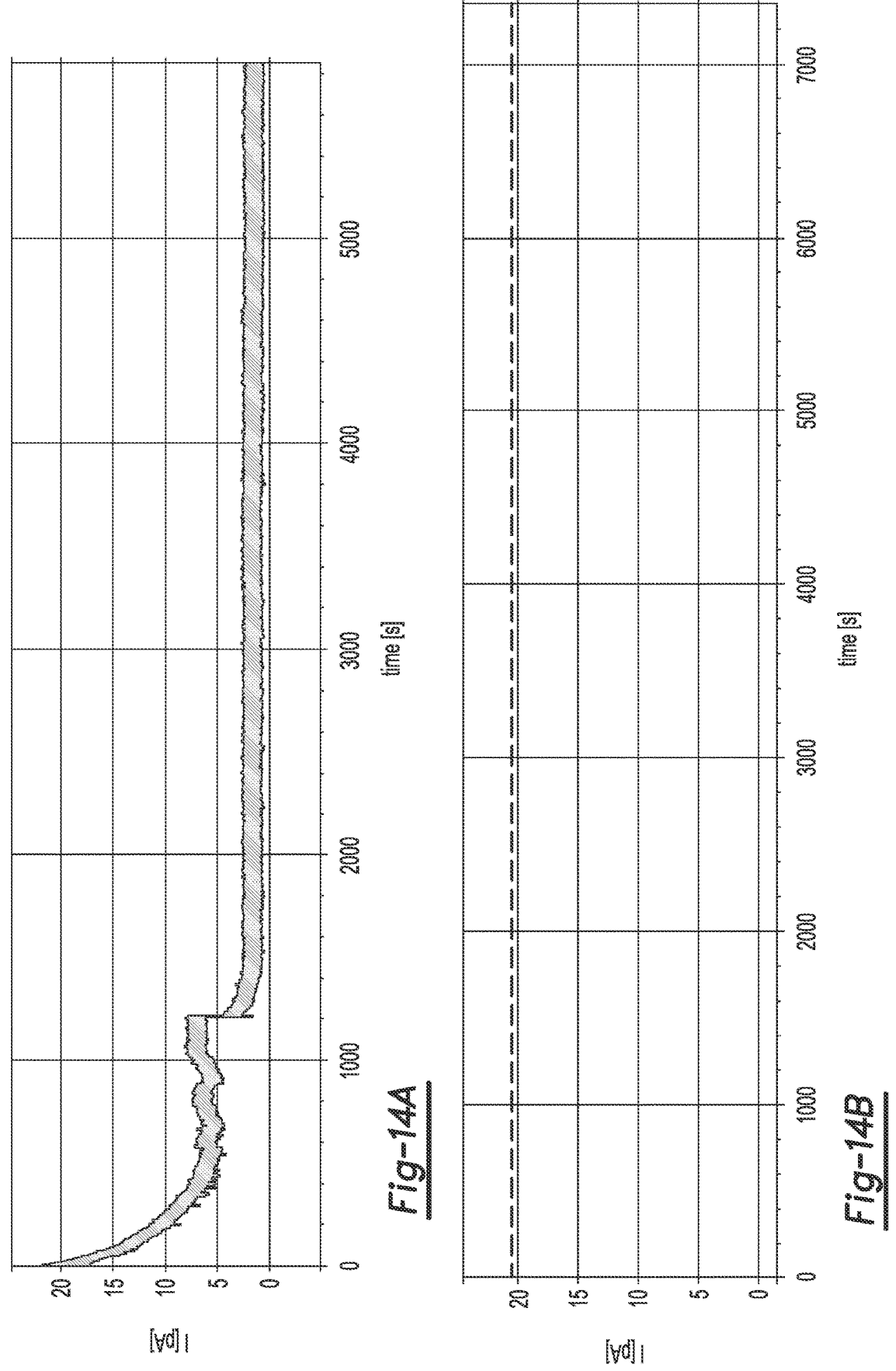
FIG. 14A is a graph depicting the current (pA, Y axis) versus time (s, X axis) for the comparative MspA pores.
FIG. 14B is a graph depicting the current (pA, Y axis) versus time (s, X axis) for the first example MspA pores.

In the third experiment, the comparative MspA pores and the first example MspA pores were tested with 150 mM $K^+Cl^-$ concentration and a cis-trans bias voltage of 50 mV. FIG. 14A plots the current (pA, Y axis) versus time (s, X axis) for the comparative MspA pores, and FIG. 14B plots the extrapolated current (pA, Y axis) versus time (s, X axis) for the first example MspA pores. The comparative pores exhibited significant current decay in the first 20 minutes, whereas the first example MspA pores exhibited no current decay.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it is to be understood that the disclosed examples may be modified. Therefore, the foregoing description is to be considered non-limiting.

What is claimed is:

1. A nanopore sensor device, comprising:
one or more cis wells;
a cis electrode;
a plurality of trans wells, each of the plurality of trans wells separated from the one or more cis wells by a membrane selected from the group consisting of a lipid bilayer, a solid-state membrane, and a liquid film material, and having a nanopore;
a plurality of trans electrodes, each of the plurality of trans electrodes associated with one of the plurality of trans wells;
a first concentration of an electrolyte within the one or more cis wells;
a second concentration of the electrolyte within the trans wells, wherein the first concentration is higher than the second concentration;
a stimulus source coupled to each of the plurality of trans electrodes either individually or via multiplexing, wherein the stimulus source is to cause current to flow through the nanopore; and
a controller coupled to the stimulus source, the controller configured to individually/selectively address the plurality of trans electrodes to cause an ionic current through the nanopore of an addressed trans electrode of the plurality of trans wells;
wherein the ionic current comprises an amount of anions of the electrolyte translocating through the nanopore to the addressed trans well that is higher than an amount of cations of the electrolyte translocating through the nanopore from the addressed trans well.

2. The nanopore sensor device as defined in claim 1, wherein the controller is further configured to cause the stimulus source to apply a unipolar electric current between the cis electrode and the addressed trans electrode of the addressed trans well of the plurality of trans wells.

3. The nanopore sensor device as defined in claim 1, wherein the nanopore has a plurality of positively charged residues on an inner surface of the nanopore.

4. The nanopore sensor device as defined in claim 3, wherein the plurality of positively charged residues on the inner surface are located at a constriction zone of the nanopore.

5. The nanopore sensor device as defined in claim 1, wherein:
the membrane is the lipid bilayer, and the lipid bilayer includes two opposing layers of phospholipids; or the membrane is the solid-state membrane, and the solid-state membrane is selected from the group consisting of silicon nitride, aluminum oxide, hafnium oxide, tantalum pentoxide, silicon oxide, polyamide, polytetrafluoroethylene, a two-component addition-cure silicone rubber, glass, and graphene; or the liquid film material is a diblock copolymer or a triblock copolymer.

6. A nanopore sensor device, comprising:
one or more cis wells;
a cis electrode;
a plurality of trans wells, each of the plurality of trans wells separated from the one or more cis wells by a membrane selected from the group consisting of a lipid bilayer, a solid-state membrane, and a liquid film material, and having a nanopore;
a plurality of trans electrodes, each of the plurality of trans electrodes associated with one of the plurality of trans wells;
a first concentration of an electrolyte within the one or more cis wells; and
a second concentration of the electrolyte within the trans wells, wherein the first concentration is higher than the second concentration;
wherein a ratio of the first concentration to the second concentration ranges from about 10:1 to about 3:1.

7. The nanopore sensor device as defined in claim 6, further comprising:
a stimulus source coupled to each of the plurality of trans electrodes either individually or via multiplexing, wherein the stimulus source is to cause current to flow through the nanopore; and
a controller coupled to the stimulus source, the controller configured to individually/selectively address the plurality of trans electrodes to cause an ionic current through the nanopore of an addressed trans electrode of the plurality of trans wells.

8. The nanopore sensor device as defined in claim 7, wherein the controller is further configured to cause the stimulus source to apply a unipolar electric current between the cis electrode and the addressed trans electrode of the addressed trans well of the plurality of trans wells.

9. The nanopore sensor device as defined in claim 6, wherein the nanopore has a plurality of positively charged residues on an inner surface of the nanopore.

10. The nanopore sensor device as defined in claim 9, wherein the plurality of positively charged residues on the inner surface are located at a constriction zone of the nanopore.

11. A nanopore sensor kit, comprising:
a nanopore sensor device, including:
one or more cis wells including a fluid inlet;
a cis electrode;
a plurality of trans wells, each of the plurality of trans wells separated from the one or more cis wells by a membrane selected from the group consisting of a lipid bilayer, a solid-state membrane, and a liquid film material, and having a nanopore;
a plurality of trans electrodes, each of the plurality of trans electrodes associated with one of the plurality of trans wells; and
a first concentration of an electrolyte within the one or more cis wells and the plurality of trans well;
a second concentration of the electrolyte to be introduced into the one or more cis wells through the fluid inlet such that the one or more cis wells contain the second concentration of the electrolyte and the plurality of trans wells contain the first concentration of the electrolyte at an initial cycle of the nanopore sensor device, wherein the second concentration is higher than the first concentration;
a stimulus source coupled to each of the plurality of trans electrodes either individually or via multiplexing, wherein the stimulus source is to cause current to flow through the nanopore; and
a controller coupled to the stimulus source, the controller configured to individually/selectively address the plurality of trans electrodes to cause an ionic current through the nanopore of an addressed trans electrode of the plurality of trans wells;
wherein the ionic current comprises an amount of anions of the electrolyte translocating through the nanopore to the addressed trans well that is higher than an amount of cations of the electrolyte translocating through the nanopore from the addressed trans well.

12. A method of detecting an ionic current to analyze a biological compound, comprising:
providing a solid-state nanopore within a membrane separating a cis well and a trans well, the solid-state nanopore having a plurality of positively charged residues on an inner surface, and the plurality of positively charged residues being selected from the group consisting of an organic positively charged species, an inorganic positively charged species, or both organic positively charged species and inorganic positively charged species;
providing an electrolyte within the cis well and the trans well; and
applying an electric current between a cis cathode at least partially exposed to the cis well and a trans anode at least partially exposed to the trans well to generate an ionic current through the nanopore,
wherein the plurality of positively charged residues of the nanopore inhibits translocation of cations from the trans well to the cis well during application of the electric current.

13. The method as defined in claim 12, wherein the plurality of positively charged residues on the inner surface are located at a constriction zone of the nanopore.

14. The method as defined in claim 12, wherein the applied electric current is a unipolar current.

15. The method as defined in claim 12, wherein the cis well comprises a higher concentration of the electrolyte than the trans well during application of the electric current.

16. A method of detecting an ionic current to analyze a biological compound, comprising:
providing a nanopore within a membrane separating a cis well and a trans well, the nanopore having a plurality of positively charged residues on an inner surface;
providing an electrolyte within the cis well and the trans well; and
applying an electric current between a cis cathode at least partially exposed to the cis well and a trans anode at least partially exposed to the trans well to generate an ionic current through the nanopore,
wherein the plurality of positively charged residues of the nanopore inhibits translocation of cations from the trans well to the cis well during application of the electric current; and wherein one of:
the electrolyte is a redox couple having a negative charge and is incorporated into a redox-inactive buffer that includes an anion having a diameter greater than a diameter of a constriction zone of the nanopore; and the electrolyte is a redox couple having a positive charge and is incorporated into a redox-inactive buffer that includes a cation having a diameter greater than a diameter of a constriction zone of the nanopore.

17. A nanopore sensor device, comprising:

one or more cis wells;

a cis electrode;

a plurality of trans wells, each of the plurality of trans wells separated from the one or more cis wells by a membrane selected from the group consisting of a lipid bilayer, a solid-state membrane, and a liquid film material, and having a nanopore;

a plurality of trans electrodes, each of the plurality of trans electrodes associated with one of the plurality of trans wells;

an electrolyte solution including:

a redox-inactive buffer that includes a redox inactive species having a diameter greater than a diameter of a constriction zone of the nanopore; and a redox couple.

18. The nanopore sensor device as defined in claim 17, further comprising:

a stimulus source coupled to each of the plurality of trans electrodes either individually or via multiplexing, wherein the stimulus source is to cause current to flow through the nanopore; and a controller coupled to the stimulus source, the controller configured to individually/selectively address the plurality of trans electrodes to cause an ionic current through the nanopore of an addressed trans electrode of the plurality of trans wells.

19. The nanopore sensor device as defined in claim 18, wherein the ionic current comprises an amount of the redox couple translocating through the nanopore to the addressed trans electrode without an amount of the redox-inactive species.

20. The nanopore sensor device as defined in claim 18, wherein the controller is further configured to apply a unipolar electric current between the cis electrode and the addressed trans electrode of the addressed trans well of the plurality of trans wells.

21. The nanopore sensor device as defined in claim 17, wherein the nanopore has a plurality of positively charged residues on an inner surface of the nanopore.

22. A nanopore sensor device, comprising:

one or more cis wells;

a cis electrode;

a plurality of trans wells, each of the plurality of trans wells separated from the one or more cis wells by a membrane selected from the group consisting of a lipid bilayer, a solid-state membrane, and a liquid film material, and having a protein nanopore with a plurality of positively charged residues on an inner surface of the protein nanopore, wherein each of the plurality of positively charged residues includes a cysteine residue functionalized with maleimide; and a plurality of trans electrodes, each of the plurality of trans electrodes associated with one of the plurality of trans wells.

23. A nanopore sensor device, comprising:

one or more cis wells;

a cis electrode;

a plurality of trans wells, each of the plurality of trans wells separated from the one or more cis wells by a membrane selected from the group consisting of a lipid bilayer, a solid-state membrane, and a liquid film material, and having a nanopore;

a plurality of trans electrodes, each of the plurality of trans electrodes associated with one of the plurality of trans wells;

a first concentration of an electrolyte within the one or more cis wells; and a second concentration of the electrolyte within the trans wells, wherein the first concentration is higher than the second concentration and wherein a ratio of the first concentration to the second concentration ranges from about 10:1 to about 3:1;

a stimulus source coupled to each of the plurality of trans electrodes either individually or via multiplexing, wherein the stimulus source is to cause current to flow through the nanopore; and a controller coupled to the stimulus source, the controller configured to individually/selectively address the plurality of trans electrodes to cause an ionic current through the nanopore of an addressed trans electrode of the plurality of trans wells;

wherein the ionic current comprises an amount of anions of the electrolyte translocating through the nanopore to the addressed trans well that is higher than an amount of cations of the electrolyte translocating through the nanopore from the addressed trans well.

*   *   *   *   *